(12) United States Patent
Sachdeva et al.

(10) Patent No.: US 7,424,370 B2
(45) Date of Patent: Sep. 9, 2008

(54) COMPUTATIONAL METHOD FOR IDENTIFYING ADHESIN AND ADHESIN-LIKE PROTEINS OF THERAPEUTIC POTENTIAL

(75) Inventors: Gaurav Sachdeva, Delhi (IN); Kaushal Kumar, Delhi (IN); Preti Jain, Delhi (IN); Samir K. Brahmachari, Delhi (IN); Srinivasan Ramachandran, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 166 days.

(21) Appl. No.: 11/052,554

(22) Filed: Feb. 7, 2005

(65) Prior Publication Data

US 2005/0288866 A1 Dec. 29, 2005

Related U.S. Application Data

(60) Provisional application No. 60/589,227, filed on Jul. 20, 2004.

(51) Int. Cl.
*G06F 17/11* (2006.01)
*G06F 17/50* (2006.01)
*G06F 19/00* (2006.01)

(52) U.S. Cl. .......................... 702/19; 530/350; 128/925
(58) Field of Classification Search .................. 702/19; 530/350
See application file for complete search history.

(56) References Cited

OTHER PUBLICATIONS

Hobohm et al. J. Mol Biol. (1995) 251,390-399.*
Zuegge et al. Gene,280, 19-26, 2001.*
Kovezdi et al. Med Res Rev 1999, 19: 249-69, 1999.*

* cited by examiner

*Primary Examiner*—Michael Borin
(74) *Attorney, Agent, or Firm*—Marshall, Gerstein & Borun LLP

(57) ABSTRACT

A computational method for identifying adhesin and adhesin-like proteins, said method comprising steps of computing the sequence-based attributes of a neural network software wherein the attributes are (i) amino acid frequencies, (ii) multiplet frequency, (iii) dipeptide frequencies, (iv),charge composition, and (v) hydrophobic composition, training the artificial neural Network (ANN) for each of the computed five attributes, and identifying the adhesin and adhesin-like proteins having probability of being an adhesin ($P_{ad}$) as $\geq 0.51$; a computer system for performing the method; and genes and proteins encoding adhesin and adhesin-like proteins.

13 Claims, 5 Drawing Sheets

Figure 1:
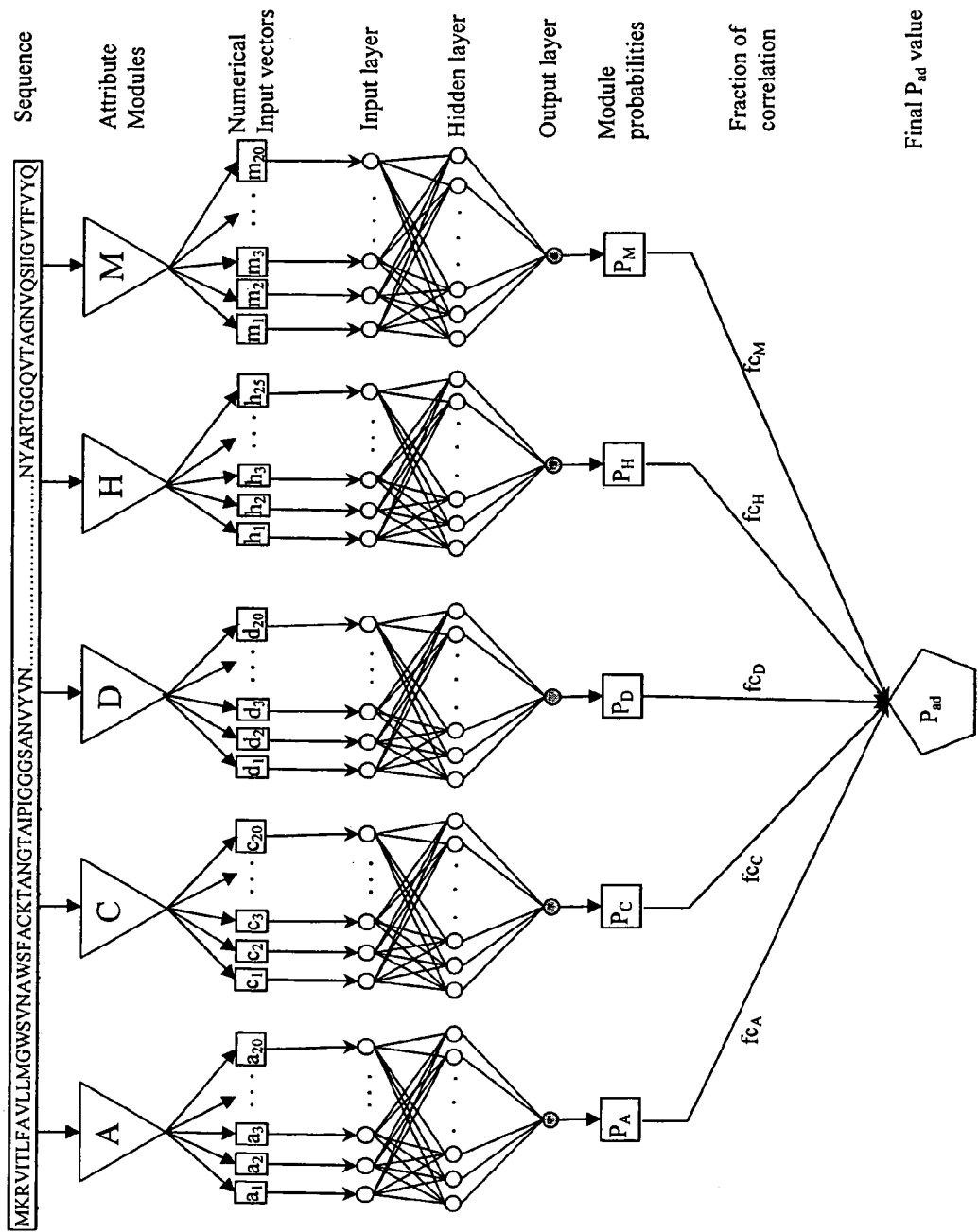

Figure 1 The Neural Network architecture

Figure 2:
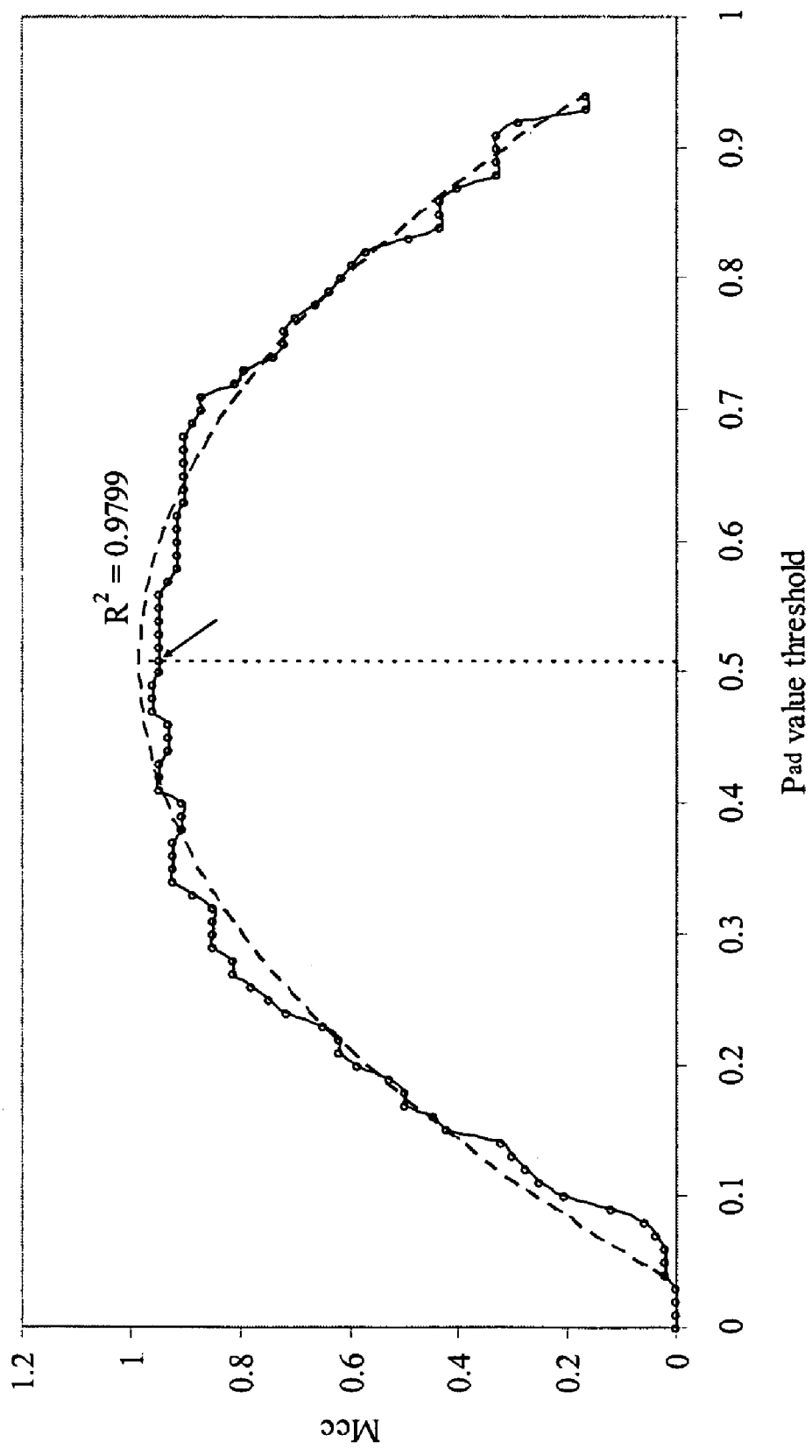

Figure 2 Assessment of SPAAN using defined test dataset.

COMPUTATIONAL METHOD FOR IDENTIFYING ADHESIN AND ADHESIN-LIKE PROTEINS OF THERAPEUTIC POTENTIAL

CROSS-REFERENCE TO OTHER APPLICATIONS

The present application claims the benefit of priority of each of the following applications: U.S., Provisional Application No. 06/589,220 filed on Jul. 20, 2004 and Indian Patent Application No. 173/DEL/2004 dated Feb. 6, 2004. The text of each of the aforementioned applications is specifically incorporated herein by reference.

The file copy of the sequence listing is submitted on a Compact-Disc Recordable (CD-R). The sequence listing is saved as an ASCII text file named 40359A.txt (2.8 1MB), which was created on May 18, 2005. The contents of the CD-R are incorporated herein by reference in its entirety.

FIELD OF THE PRESENT INVENTION

A computational method for identifying adhesin and adhesin-like proteins; computer system for performing the method; and genes and proteins encoding adhesin and adhesin-like proteins.

BACKGROUND AND PRIOR ART OF THE PRESENT INVENTION

The progress in genome sequencing projects has generated a large number of inferred protein sequences from different organisms. It is expected that the availability of the information on the complete set of proteins from infectious human pathogens will enable us to develop novel molecular approaches to combat them. A necessary step in the successful colonization and subsequent manifestation of disease by microbial pathogens is the ability to adhere to host cells.

Microbial pathogens encode several proteins known as adhesins that mediate their adherence to host cell surface receptors, membranes, or extracellular matrix for successful colonization. Investigations in this primary event of host-pathogen interaction over the past decades have revealed a wide array of adhesins in a variety of pathogenic microbes. Presently, substantial information on the biogenesis of adhesins and the regulation of adhesin factors is available. One of the best understood mechanisms of bacterial adherence is attachment mediated by pili or fimbriae. Several afimbrial adhesins also have been reported. In addition, limited knowledge on the target host receptors also has been gained (Finlay, B. B. and Falkow, S 1997).

New approaches to vaccine development focus on targeting adhesins to abrogate the colonization process (Wizemann, et al 1999). However, the specific role of particular adhesins has been difficult to elucidate. Thus, prediction of adhesins or adhesin-like proteins and their functional characterization is likely to aid not only in deciphering the molecular mechanisms of host pathogen interaction but also in developing new vaccine formulations, which can be tested in suitable experimental model systems.

One of the best understood mechanisms of bacterial adherence is attachment mediated by pili or fimbriae. For example, FimH and PapG adhesins of *Escherichia coli* (Maurer, L., Orndorff, P. (1987), Bock, K., et al. (1985). Other examples of pili group adhesins include type IV pili in *Pseudomonas aeruginosa*, *Neisseria* species, *Moraxella* species, Enteropathogenic *Escherichia coli* and *Vibrio cholerae* (Sperandio V et al (1996). Several afimbrial adhesins are HMW proteins of *Haemophilus influenzae* (van Schilfgaarde 2000), the filamentous hemagglutinin, pertactin, of *Bordetella pertussis* (Bassinet et al 2000), the BabA of *H. pylori* (Yu J et al 2002) and the YadA adhesin of *Yersinia enterocolitica* (Neubauer et al 2000). The intimin receptor protein (Tir) of Enteropathogenic *E. coli* (EPEC) is another type of adhesin (Ide T et al 2003). Other class of adhesins includes MrkD protein of *Kleibsella pneumoniae*, Hia of *H. influenzae* (St Geme et al 2000), Ag I/II of *Streptococcus mutans* and SspA, SspB of *Streptococcus gordonii* (Egland et al 2001), FnbA, FnbB of *Staphylococcus aureus* and SfbI, protein F of *Streptococcus pyogenes*, the PsaA of *Streptococcus pneumoniae* (De et al 2003).

A known example of adhesins approved as vaccine is the acellular pertussis vaccine containing FHA and pertactin against *B. pertussis* the causative agent of whooping cough (Halperin, S et al 2003). Immunization with FimH is being evaluated for protective immunity against pathogenic *E. coli* (Langermann S et al 2000), in *Streptococcus pneumoniae*, PsaA is being investigated as a potential vaccine candidate against pneumococcal disease (Rapola, S et al 2003). Immunization results with BabA adhesin showed promise for developing a vaccine against *H. pylori* (Prinz, C et al 2003). A synthetic peptide sequence anti-adhesin vaccine is being evaluated for protection against *Pseudomonas aeruginosa* infections.

Screening for adhesin and adhesin like proteins by conventional experimental method is laborious, time consuming and expensive. As an alternative, homology search is used to facilitate the identification of adhesins. Although, this procedure is useful in the analysis of genome organization (Wolf et al 2001) and of metabolic pathways. (Peregrin-Alvarez et al 2003, Rison et al 2002), it is somewhat limited in allowing functional predictions when the homologues are not functionally characterized or the sequence divergence is high. Assignment of functional roles to proteins based on this technique has been possible for only about 60% of the predicted protein sequences (Fraser et al 2000). Thus, we explored the possibility of developing a non-homology method based on sequence composition properties combined with the power of the Artificial Neural Networks to identify adhesins and adhesin-like proteins in species belonging to wide phylogenetic spectrum.

Twenty years ago, Nishikawa et al carried out some of the early attempts to classify proteins into different groups based on compositional analysis (Nishikawa et al 1983). More recently, the software PropSearch was developed for analyzing protein sequences where conventional alignment tools fail to identify significantly similar sequences (Hobohm, U. and Sander, C 1995). PropSearch uses 144 compositional properties of protein sequences to detect possible structural or functional relationships between a new sequence and sequences in the database. Recently the compositional attributes of proteins have been used to develop softwares for predicting secretory proteins in bacteria and apicoplast targeted proteins in *Plasmodium falciparum* by training Artificial Neural Networks (Zuegge et al 2001).

Zuegge et al have used the 20 amino acid compositional properties. Their objective was to extract features of apicoplast targeted proteins in *Plasmodium falciparum*. This is distinct from our software SPAAN that focuses on adhesins and adhesin-like proteins involved in host-pathogen interaction.

Hobohm and Sander have used 144 compositional properties including isoelectric point and amino acid and dipeptide composition to generate hypotheses on putative functional role of proteins that are refractory to analysis using other sequence alignment based approaches like BLAST and FASTA. Hobohm and Sander do not specifically address the issue of adhesins and adhesin-like proteins, which is the focus of SPAAN. Nishikawa et al had originally attempted to classify proteins into various functional groups. This was a curiosity driven exercise but eventually lead to the development of a software to discriminate extra-cellular proteins from intracellular proteins. This work did not address the issue of adhesins and adhesin-like proteins, which is the focus of SPAAN.

Thus, none of the aforementioned research groups have been able to envisage the methodology of the instant application. The inventive method of this application provides novel proteins and corresponding gene sequences.

Adhesins and adhesin-like proteins mediate host-pathogen interactions. This is the first step in colonization of a host by microbial pathogens. Attempts Worldwide are focused on designing vaccine formulations comprising adhesin proteins derived from pathogens. When immunized, host will have its immune system primed against adhesins for that pathogen. When a pathogen is actually encountered, the surveillance mechanism will recognize these adhesins, bind them through antigen-antibody interactions and neutralize the pathogen through complement mediate cascade and other related clearance mechanisms. This strategy has been successfully employed in the case of Whooping cough and is being actively pursued in the case of Pneumonia, Gastric Ulcer and Urinary tract infections.

OBJECTS OF THE PRESENT INVENTION

The main object of the present invention is to provide a computational method for identifying adhesin and adhesin-like proteins of therapeutic potential.

Another object of invention is to provide a method for screening the proteins with unique compositional characteristics as putative adhesins in different pathogens.

Yet, another object of the invention is providing the use of gene sequences encoding the putative adhesin proteins useful as preventive therapeutics.

SUMMARY OF THE PRESENT INVENTION

A computational method for identifying adhesin and adhesin-like proteins, said method comprising steps of computing the sequence-based attributes of protein sequences using five attribute modules of software SPAAN, (i) amino acid frequencies, (ii) multiplet frequency, (iii) dipeptide frequencies, (iv) charge composition, and (v) hydrophobic composition, training the artificial neural Network (ANN) for each of the computed five attributes, and identifying the adhesin and adhesin-like proteins having probability of being an adhesin ($P_{ad}$) as $\geq 0.51$; a computer system for performing the method; and genes and proteins encoding adhesin and adhesin-like proteins

DETAILED DESCRIPTION OF THE PRESENT INVENTION

Accordingly, the present invention relates to a computational method for identifying adhesin and adhesin-like proteins, said method comprising steps of computing the sequence-based attributes of protein sequences using five attribute modules of software SPAAN, (i) amino acid frequencies, (ii) multiplet frequency, (iii) dipeptide frequencies, (iv) charge composition, and (v) hydrophobic composition, training the artificial neural Network (ANN) for each of the computed five attributes, and identifying the adhesin and adhesin-like proteins having probability of being an adhesin ($P_{ad}$) as $\geq 0.51$; a computer system for performing the method; and genes and proteins encoding adhesin and adhesin-like proteins In an embodiment of the present invention, wherein the invention relates to a computational method for identifying adhesin and adhesin-like proteins, said method comprising steps of:
  a. computing the sequence-based attributes of protein sequences using five attribute modules of a neural network software, wherein the attributes are software, (i) amino acid frequencies, (ii) multiplet frequency, (iii) dipeptide frequencies, (iv) charge composition, and (v) hydrophobic composition,
  b. training the artificial neural Network (ANN) for each of the computed five attributes, and
  c. identifying the adhesin and adhesin-like proteins having probability of being an adhesin ($P_{ad}$) as $\geq 0.51$.

In another embodiment of the present invention, wherein the invention relates to a method wherein the protein sequences is obtained from pathogens, eukaryotes, and multicellular organisms.

In an embodiment of the present invention, wherein the invention relates to a method, wherein the protein sequences are obtained from the pathogens selected from a group of organisms comprising *Escherichia coli, Haemophilus influenzae, Helicobacter pylori, Mycoplasma pneumoniae, Mycobacterium tuberculosis, Rickettsiae prowazekii, Porphyromonas gingivalis, Shigella flexneri, Streptococcus mutans, Streptococcus pneumoniae, Neisseria men ingitides, Streptococcus pyogenes, Treponema pallidum* and Severe Acute Respiratory Syndrome associated human coronavirus (SARS).

In yet another embodiment of the present invention, wherein the method of the invention is a non-homology method.

In still another embodiment of the present invention, wherein the invention relates to the method using 105 compositional properties of the sequences.

In still another embodiment of the present invention, wherein the invention relates to a method showing sensitivity of at least 90%.

In still another embodiment of the present invention, wherein the invention relates to the method showing specificity of 100%.

In still another embodiment of the present invention, wherein the invention relates to a method identifying adhesins from distantly related organisms.

In still another embodiment of the present invention, wherein the invention relates to the neural network has multi-layer feed forward topology, consisting of an input layer, one hidden layer, and an output layer.

In still another embodiment of the present invention, wherein the invention relates to the number of neurons in the input layer are equal to the number of input data points for each attribute.

In still another embodiment of the present invention, wherein the invention relates to the "$P_{ad}$" is a weighted linear sum of the probabilities from five computed attributes. In still another embodiment of the present invention, wherein the invention relates to each trained network assigns a probability value of being an adhesin for the protein sequence.

In still another embodiment of the present invention, wherein the invention relates to a computer system for performing the method of claim 1, said system comprising a central processing unit, executing SPAAN program, giving probabilities based on different attributes using Artificial Neural Network and in built other programs of assessing attributes, all stored in a memory device accessed by CPU, a display on which the central processing unit displays the screens of the above mentioned programs in response to user inputs; and a user interface device.

In still another embodiment of the present invention, wherein the invention relates to a set of 274 annotated genes encoding-adhesin and adhesin-like proteins, having SEQ ID Nos. 385 to 658.

In still another embodiment of the present invention, wherein the invention relates to a set of 105 hypothetical genes encoding adhesin and adhesin-like proteins, having SEQ. ID Nos. 659 to 763.

In still another embodiment of the present invention, wherein the invention relates to a set of 279 annotated adhesin and adhesin-like proteins of SEQ ID Nos. 1 to 279.

In still another embodiment of the present invention, wherein the invention relates to a set of 105 hypothetical adhesin and adhesin-like proteins of SEQ ID Nos. 280 to 384.

One more embodiment of the present invention, wherein the invention also relates to a fully connected multilayer feed forward Artificial Neural Network based on the computational method as claimed in claim 1, comprising of an input layer, a hidden layer and an output layer which are connected in the said sequence, wherein each neuron is a binary digit number and is connected to each neuron of the subsequent layer for identifying adhesin or adhesin like proteins, wherein the program steps comprise: [a] feeding a protein sequence in FASTA format; [b] processing the sequence obtained in step [a] through the 5 modules named A, C, D, H and M, wherein attribute. A represents an amino acid composition, attribute C represents a charge composition, attribute D represents a dipeptide composition of the 20 dipeptides [NG, RE, TN, NT, GT, TT, DE, ER, RR, RK, RI, AT, TS, IV, SG, GS, TG, GN, VI and HR], attribute H represents a hydrophobic composition and attribute M represents amino acid frequencies in multiplets to quantify 5 types of compositional attributes of the said protein sequence to obtain numerical input vectors respectively for each of the said attributes wherein the sum of numerical input vectors is 105; [c] processing of; the numerical input vectors obtained in step [b] by,the input neuron layer to obtain signals, wherein the number of neurons is equal to the number of numerical input vectors for each attribute; [d] processing of signals obtained from step [c] by the hidden layer to obtain synaptic weighted signals, wherein the optimal number of neurons in the hidden layer was determined through experimentation for minimizing the error at the best epoch for each network individually; [e] delivering synaptic weighted signals obtained from step [d] to the output layer for assigning of a probability value for each protein sequence fed in step [a] as being an adhesin by each network module; [f] using the individual probabilities obtained from step [e] for computing the final probability of a protein sequence being an adhesin denoted by the $P_{ad}$ value, which is a weighted average of the individual probabilities obtained from step [e] and the associated fraction of correlation which is a measure of the strength of the prediction.

In still another embodiment of the present invention, wherein the input neuron layer consists of a total of 105 neurons corresponding to 105 compositional properties.

In still another embodiment of the present invention, wherein the hidden layer comprises of neurons represented as 30 for amino acid frequencies, 28 for multiplet frequencies, 28 for dipeptide frequencies, 30 for charge composition and 30 for hydrophobic composition.

In still another embodiment of the present invention, wherein the output layer comprises of neurons to deliver the output values as probability value for each protein sequence.

Identification of novel adhesins and their characterization are important for studying host-pathogen interactions and testing new vaccine formulations. We have employed Artificial Neural Networks to develop an algorithm SPAAN (Software for Prediction of Adhesin and Adhesin-like proteins using Neural Networks) that can identify adhesin proteins using 105 compositional properties of a protein sequence. SPAAN could correctly predict well characterized adhesins from several bacterial species and strains. SPAAN showed 89% sensitivity and 100% specificity in a test data set that did not contain proteins in the training set. Putative adhesins identified by the software can serve as potential preventive therapeutics.

The present invention provides a novel computational method for identifying adhesin and adhesin-like proteins of therapeutic potential. More particularly, the present invention relates to candidate genes for these adhesins. The invention further provides new leads for development of candidates genes, and their encoded proteins in their functional relevance to preventive approaches. This computational method involves calculation of several sequence attributes and their subsequent analyses lead to the identification of adhesin proteins in different pathogens. Thus, the present invention is useful for identification of the adhesin proteins in pathogenic organisms. The adhesin proteins from different genomes constitute a set of candidates for functional characterization through targeted gene disruption, microarrays and proteomics. Further, these proteins constitute a set of candidates for further testing in development of preventive therapeutics. Also, are provided the genes encoding the candidate adhesin proteins.

The present method offers novelty in the principles used and the power of Neural Networks to identify new adhesins compared to laborious and time consuming conventional methods. The present method is based on compositional properties of proteins instead of sequence alignments. Therefore this method has the ability to identify adhesin and adhesin like proteins from bacteria belonging to a wide phylogenetic spectrum. The predictions made from this method are readily verifiable through independent analysis and experimentation. The invention has the potential to accelerate the development of new preventive therapeutics, which currently requires high investment in terms of requirement of skilled labor and valuable time.

The present invention relates to a computational method for the identification of candidate adhesin proteins of therapeutic potential. The invention particularly describes a novel method to identify adhesin proteins in different genomes of pathogens. These adhesin proteins can be used for developing preventive therapeutics.

Accordingly, a computational method for identifying adhesin and adhesin-like proteins of therapeutic potential which comprises calculation of 105 compositional properties under the five sequence attributes, namely, Amino Acid frequency, Multiplet frequency, dipeptide frequency, charge composition and hydrophobic composition; and then training Artificial Neural Network (ANN, Feed Forward Error Back Propagation) using these properties for differentiating between adhesin and non-adhesin class of proteins. This computational method involves quantifying 105 compositional attributes of query proteins and qualifying them as adhesins or non-adhesins by a $P_{ad}$ value (Probability of being an adhesin). The present invention is useful for identification of adhesin and adhesin-like proteins in pathogenic organisms.

These newly identified adhesin and adhesin-like proteins constitute a set-of candidates for development of new preventive therapeutics that can be tested in suitable experimental model systems readily. In addition, the genes encoding the candidate adhesin and adhesin-like proteins are provided.

The invention provides a set of candidate adhesin and adhesin-like proteins and their coding genes for further evaluation as preventive therapeutics. The method of invention is based on the analysis of protein sequence attributes instead of sequence patterns classified to functional domains. Present method is less dependent on sequence relationships and therefore offers the potential power of identifying adhesins from distantly related organisms. The invention provides a computational method, which involves prediction of adhesin and adhesin-like proteins using Artificial Neural Networks. The proteins termed adhesin were found to be predicted with a high probability ($P_{ad} \geq 0.51$) in various pathogens. Some adhesin sequences turned out to be identical or homologous to proteins that are antigenic or implicated in virulence. By this approach, proteins could be identified and short-listed for further testing in development of new vaccine formulations to eliminate diseases caused by various pathogenic organisms.

DESCRIPTION OF TABLES

Table 1: Output file format given by SPAAN.
Table 2: Organism Name, Accession number, Number of base pairs, Date of release and Total number of proteins.
Table 3. Prediction of well characterized adhesins from various bacterial pathogens using SPAAN.
Table 4. Analysis of predictions made by SPAAN on genome scans of a few selected pathogenic organisms.
Table 5: GI numbers and Gene IDs of new putative adhesins predicted by SPAAN in the genomes listed in Table 2.
Table 6: GI numbers and Gene IDs of hypothetical proteins predicted as putative adhesins by SPAAN in the genomes listed in Table 2.
Table 7: The list of 198 adhesins found in bacteria

BRIEF DESCRIPTION OF THE ACCOMPANYING DRAWINGS

Figure 3:
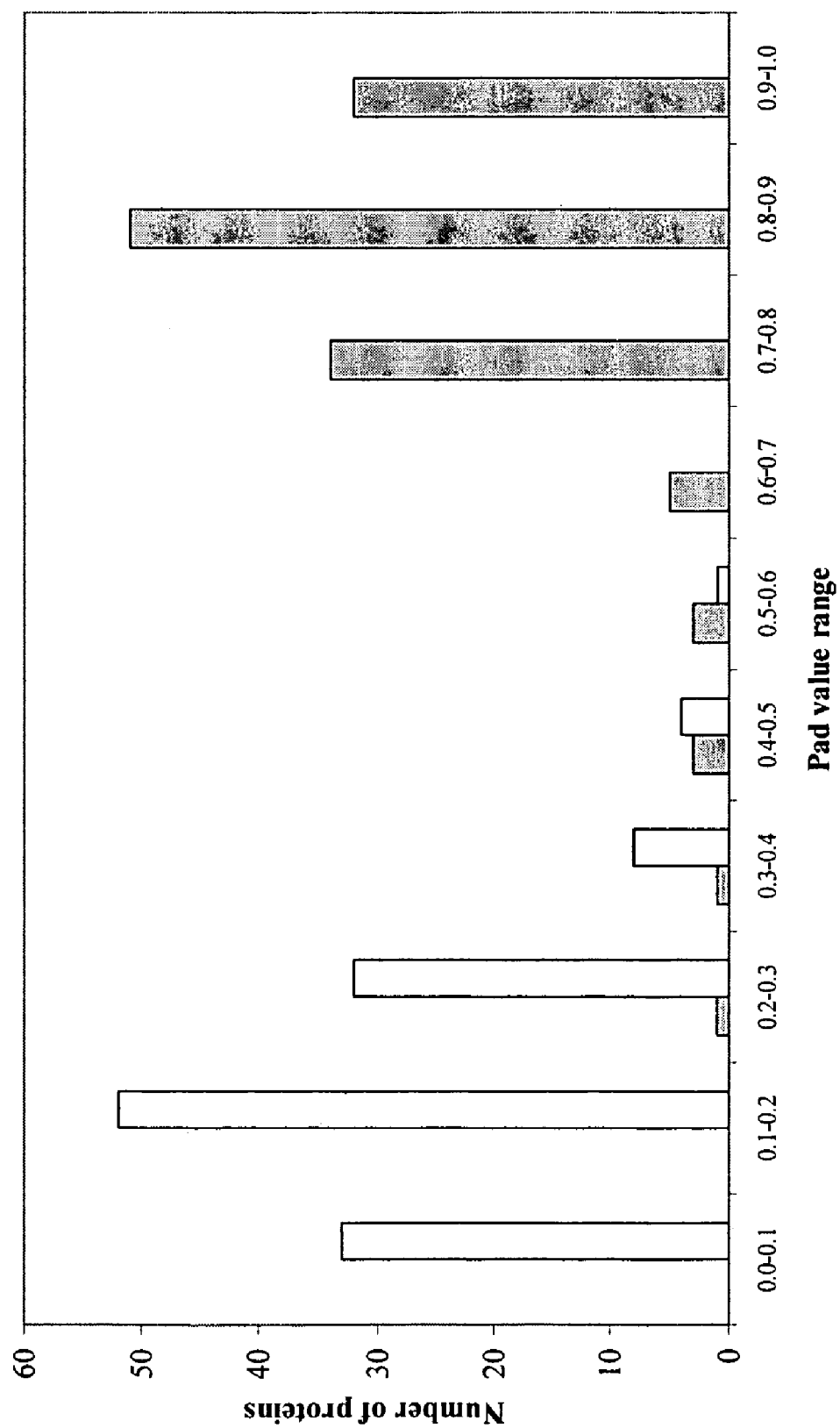
Figure 3:
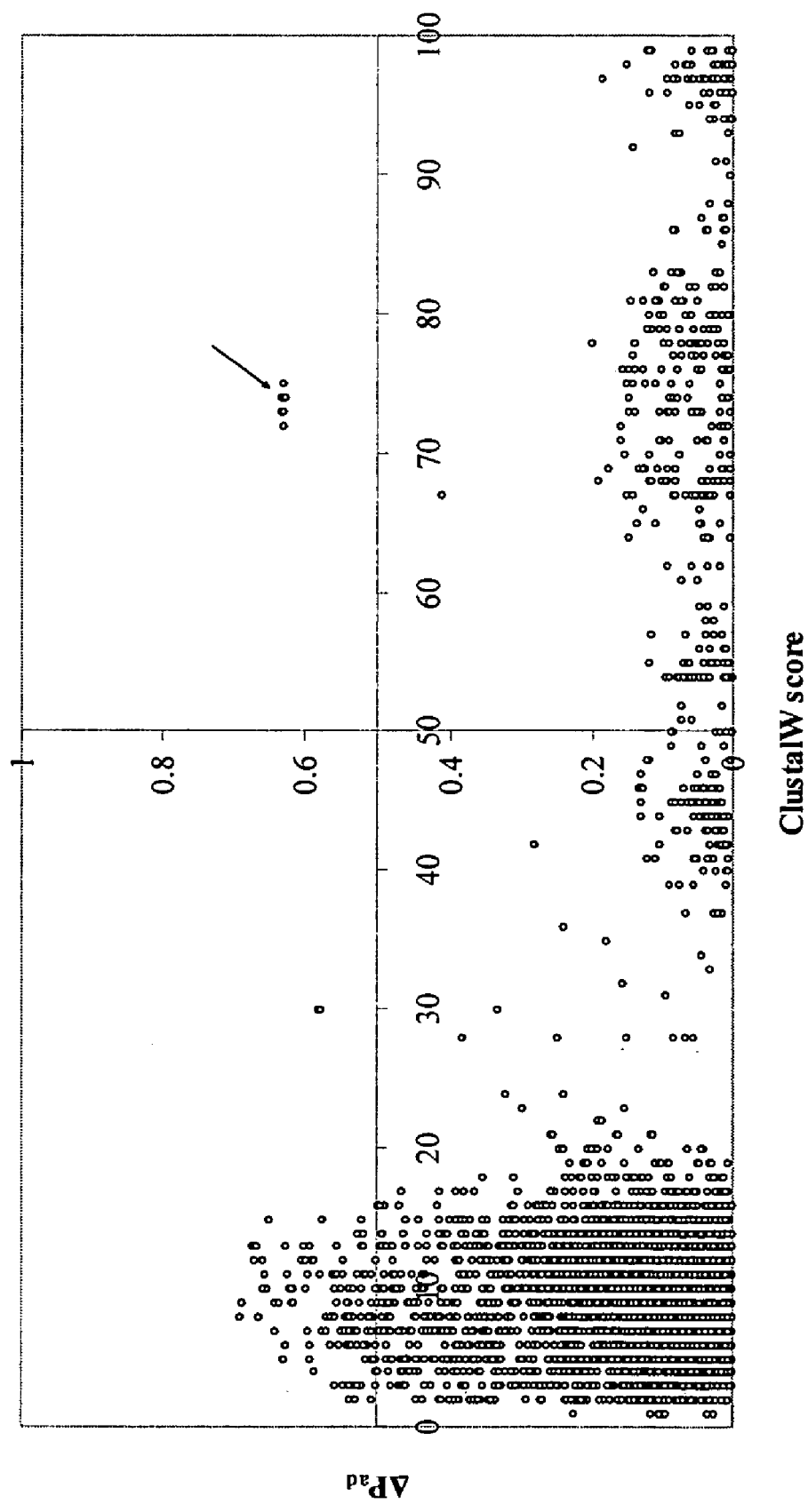

FIG. 1, shows the Neural Network architecture
FIG. 2 shows assessment of SPAAN using defined test dataset.
FIG. 3(*a*) shows Histogram plots of the number of proteins in the various $P_{ad}$ value ranges are shown. (*b*) Pairwise sequence relationships among the adhesins were determined using CLUSTAL W and plotted on X-axis. Higher scores indicate similar pairs. (*c*) plot for non-adhesins. Data are plotted in the 4 quadrant format for clear inspection.

Software program was written in C Language and operated on Red Hat Linux 8.0 operating system. The computer program accepts input protein sequences in FastA format and produces a tabulated output. The output Table contains one row for each protein listing the probability outputs of each of the five modules, a weighted average probability of these five modules ($P_{ad}$), and the function of the protein as described in the input sequence file. This software is called SPAAN (A Software for Prediction of Adhesins and Adhesin-like proteins using Neural Networks) and a software copyright has been filed. Although this software has multiple modules, the running of these modules have been integrated and automated. The user only needs to run one command.

AAcompo.c:
  Input: File containing protein sequences in the fasta format.
  Output: File containing frequencies of all 20 AAs for each protein in one row.
charge.c:
  Input: File containing protein sequences in the fasta format.
  Output: File containing frequency of charged amino acids (R, K, E and D) and moments (up to 18th order) of the positions of charged amino acids.
hdr.c:
  Input: File containing protein sequences in the fasta format.
  Output: File containing frequencies of 5 groups of amino acids formed on the basis their Hydrophobicity and moments of their positions up to 5th order.
multiplets.c:
  Input: File containing protein sequences in the fasta format.
  Output: File containing fractions of multiplets of each of the 20 amino acids.
quetydipep.c:
  Input: File. 1 containing protein sequences in the fasta format.
    File.2 containing list of the significant dipeptides in dipeptide analysis.
  Output: File containing frequencies of the dipeptides listed in the input File.2 for each protein in the input File. 1.
train.c:
  Input: File containing following specifications
    1. Number of input and output parameters.
    2. Number of nodes in the hidden layers.
    3. Names of the training, validate and test data files.
    4. Learning rate, coefficient of moment.
    5. Maximum number of cycles for training.
  Output: Outputs are as follows.
    1. Output of the trained NN for the test data set.
    2. Values of the weight connections in the trained NN.
    3. Some extra information about training.
recognize.c:
  Input: File containing following specifications
    1. Number of input and output parameters.
    2. Number of nodes in the hidden layers.
    3. Names of the query input file.
    4. Name of the file containing values of the weight connections for trained NN.
    5. Name of the output file.
  Output: Outputs for the query entries calculated by the trained NN.
standard.c:
  Input: File containing protein sequences in fasta format.
  Output: File containing protein sequences in fasta format with all the new line characters removed lying within a sequence.
filter.c:
  Input: File containing protein sequences in fasta format.
  Output: File containing protein sequences from the input except those which are short in length (<50 AAs) and which contain any amino acid other than the 20 known amino acids.

The Five Attributes:

Amino Acid Frequencies
  Amino acid frequency $f_i$=(counts of ith amino acid in the sequence)/1; i, =1 . . . 20, 1 is the length of the protein.

Multiplet Frequency
  Multiplets are defined as homopolymeric stretches $(X)_n$ where X is any of the 20 amino acids and n is an integer >2.

After identifying all the multiplets, the frequencies of the amino acids in the multiplets were computed as $f_i(m)$=(counts of $i^{th}$ amino acid occurring as multiplet)/1

Dipeptide Frequencies

The frequency of a dipeptide (i, j) $f_{ij}$=(counts of $ij^{th}$ dipeptide)/(total dipeptide counts); i, j ranges from 1 to 20.

It has been found that dipeptide repeats in proteins are important for functional expression of the clumping factor present on *Staphylococcus aureus* cell surface that binds to fibrinogen (Hartford et al 1999). Thus we included the dipeptide frequency module. The total number of dipeptides is 400. For optimal training of Neural Network, the ratio of total number of input vectors to the total number of weight connections must be around 2 to avoid over fitting (Andrea et al). Therefore, we identified the dipeptides whose frequencies in the adhesin data set (469 proteins, see database construction) were significantly different from that in the non-adhesin dataset (703 proteins) using t-test. The frequencies of top 20 dipeptides (when arranged in the descending order of the p-values of t-test), were fed to the Neural Network. These dipeptides were (using single letter IUPAC-IUB code) NG, RE, TN, NT, GT, TT, DE, ER, RR, RK, RI, AT, TS, IV, SG, GS, TG, GN, VI, AND HR. With frequency inputs for 20 dipeptides and 28 neurons in the 2nd layer, the total number of weight connections is 588, and is in keeping with the criterion of avoiding over fitting.

Charge Composition

The input frequency of charged amino acids (R, K, E and D considering the ionization properties of the side chains at pH 7.2) given by $f_c$=(counts of charged amino acids)/1 Further, information on the characteristics of the distribution of the charged amino acids in a given protein sequence was provided by computing the moments of the positions of the occurrences of the charged amino acids. Since moments characterize the patterns of distribution such as skewness and kurtosis (sharpness of the peak) we have used them to represent the distribution patterns of the charged residues in the sequence.

The general expression to compute moments of a given order; say 'i' is $$M_r = r^{th} \text{ order moment of the positions of charged amino acids}$$
$$= \sum \frac{(X_i - X_m)^r}{N}$$

Where, $X_m$=mean of all positions of charged amino acids
$X_i$=position of $i^{th}$ charged amino acid
N=number of charged amino acids in the sequence The moments $2^{nd}$ to $19^{th}$ order were used to train the ANN constituting a total 20 inputs in addition to frequency of charged amino acids and the length of the protein. The upper limit of $19^{th}$ order was set based on assessments of sensitivity and specificity on a small dataset of adhesins and non-adhesins. Moments of order greater than 19 were not useful in improvement of performance.

Hydrophobic Composition

A given protein sequence was digitally transformed using the hydrophobic scores of the amino acids according to Brendel et al. (43). The scores for five groups of amino acids: (−8 for K, E, D, R), (−4 for S, T, N, Q), (−2 for P, H), (+1 for A, G, Y, C, W), (+2 for L, V, I, F, M).

Following inputs were given for each of the group
(a) $f_i$=(counts of $i^{th}$ group)/(total counts in the protein); i ranges from 1 to 5
(b) $m_{ji}$=$j^{th}$ order moment of positions of amino acids in $i^{th}$ group; j ranges from 2 to 5.

A total of 25 inputs representing the hydrophobic composition of a protein were fed to the Neural Network. The rationale for using moments was same as described in the section on charge composition inputs.

Taken together a total of 105 compositional properties of a given protein sequence Were used to predict their adhesin characteristics.

The software PropSearch uses 144. compositional properties of protein sequences to detect possible structural or functional relationships between a new sequence and sequences in the database (Hobohm and Sander 1995). The approach defines protein sequence dissimilarity (or distance) as a weighted sum of differences of compositional properties such as singlet and doublet amino acid composition, molecular weight, isoelectric point (protein property search or PropSearch). Compositional properties of proteins have also been used for predicting secretory proteins in bacteria and apicoplast targeted proteins in Plasmodium falciparum (Zuegge, et al. 2001). The properties used here are statistical methods, principal component analysis, self-organizing maps, and supervised neural networks. In SPAAN, we have used 105 compositional properties in the five modules viz. Amino Acid frequencies, Multiplet frequencies, Dipeptide frequencies, Charge composition, Hydrophobic composition. The total of 105 properties used in SPAAN are 20 for Amino acid frequencies, 20 for Multiplets frequencies, 20 for Dipeptide frequencies (Top 20 significant dipeptides are used, based on t-test), 20 for Charge composition (frequency of charged amino acids (R, K, E and D) and moments of 2nd to 19th order), and 25 for Hydrophobic composition (Amino acids were classified into five groups (−8 for K, E, D, R), (−4 for S, T, N, Q), (−2 for P, H), (+1 for A, G, Y, C, W), (+2 for L, V, I, F, M). A total of 25 inputs consisted of the following: Frequency of each group, Moments of positions of amino acids in each group from 2nd to 5th order.

Neural Network

A feed forward error back propagation Neural Network was used. The program is a kind gift from Charles W. Anderson, Department of Computer Science, Colorado State University, Fort Collins, Colo. 80523, anderson@cs.colostate.edu Neural Network Architecture The Neural Network used here has a multi-layer feed-forward topology. It consists of an input layer, one hidden layer and an output layer. This is a 'fully-connected' Neural Network where each neuron i is connected to each unit j of the next layer (FIG. 1). The weight of each-connection is denoted by $w_{ij}$. The state $I_i$ of each neuron in the input layer is assigned directly from the input data, whereas the states of hidden layer neurons are computed by the sigmoid function, $$h_j=1/(1+\exp-(w_{j0}+\Sigma w_{ij}I_i)),$$

where, $w_{j0}$ is the bias weight

The back propagation algorithm was used to minimize the differences between the computed output and the desired output. Ten thousand cycles (epochs) of iterations are performed. Subsequently, the best epoch with minimum error was identified. At this point the network produces approximate target values for a given input in the training set.

A network was trained optimally for each attribute. Thus five networks were prepared. The schematic diagram (FIG. 1) shows the procedure adopted. The number of neurons in the input layer was equal to the number of input data points for each attribute (for example 20 neurons for 20 numerical input vectors of the amino acid composition attribute). The optimal number of neurons in the hidden layer was determined through experimentation for minimizing the error at the best epoch for each network individually. An upper limit for the total number of weight connections was set to half of the total number of input vectors to avoid over fitting as suggested previously (Andrea et al).

Computer programs to compute individual compositional attributes were written in C and executed on a PC under Red Hat Linux ver 7.3 or 8.0. The network was trained on the training set, checks error and optimizes using the validate set through back propagation. The validate set was different from the training set. Since, the number of well annotated adhesins were not many, we used the 'validate set' itself as test set for preliminary evaluation of the performance and to obtain the fraction of correlation to compute the weighted average probability ($P_{ad}$ value) described in the next section. The training set had 367 adhesins and 580 non-adhesins. The validate set had 102 adhesins and 123 non-adhesins. The adhesins were qualified with a digit '1' and the non-adhesins were qualified with a digit '0'.

During predictions, the network is fed with new data from the sequences that were not part of training set. Each network assigns a probability value of being an adhesin to a given sequence. The final probability is computed as described in the next section.

Probability of being an Adhesin, the $P_{ad}$ Value

Query proteins are processed modularly through network trained for each attribute. Thus, five probability outputs are obtained. Final prediction was computed using the following expression which is a weighted linear sum of the probabilities from five modules:

$$P_{ad}=\frac{(P_A*fc_A+P_C*fc_C+P_D*fc_D+P_H*fc_H+P_M*fc_M)}{(fc_A+fc_C+fc_D+fc_H+fc_M)}$$

$P_i$=Probability from i module, $fc_i$=fraction of correlation of i module of the trained Neural Network, Where i=A (Amino acid frequencies), C (Charge composition), D (Dipeptide frequencies), H (Hydrophobic composition), or M (Multiplet frequencies).

The fraction of correlation $fc_i$ represents the fraction of total entries that were correctly predicted. ($P_{i,adhesin}>0.5$ and $P_{i,non-adhesin}<0.5$) by the trained network on the test set used in preliminary evaluation (Charles Anderson).

Neural Network

A feed forward error back propagation Neural Network was used. The program was downloaded from the web site with permission from the author, Charles W. Anderson, Department of Computer Science, Colorado State University, Fort Collins, Colo. 80523, anderson@cs.colostate.edu Statistical Analysis All statistical procedures were carried out using Microsoft Excel (Microsoft Corporation Inc. USA).

Sequence Analysis

Homology analysis was carried out using CLUSTAL W (Thompson et al 1994), BLAST (Altschul et al 1990), CDD (conserved domain database) search (Marchler-Bauer et al 2002).

The whole genome sequences of microbial pathogens present new opportunities for the development of clinical applications such as diagnostics and vaccines. The present invention provides new leads for the development of candidate genes, and their encoded proteins in their functional relevance to preventive therapeutics.

The protein sequences of both the classes, i.e. adhesin and non-adhesin, were downloaded from the existing database (National Centre for Biotechnology Information (NCBI), USA). A total of 105 compositional properties under the five sequence attributes namely, amino acid composition, multiplet composition, dipeptide composition, charge composition and hydrophobic composition were computed by computer programs written in C language. The attributes were computed for all the proteins in both the databases. The sequence-based attributes were then used to train Artificial Neural Network for each of the protein attributes. Adhesins were qualified, by the digit '1' and non-adhesins were qualified by the digit '0'. Finally each trained Artificial Neural Network was used to identify potential adhesins which can be envisaged to be useful for the development of preventive therapeutics against pathogenic infections. Accordingly, the invention provides a computational method for identifying adhesin and adhesin-like proteins of therapeutic potential, which comprises:

1. preparing two comprehensive data-sets of adhesin and non-adhesin proteins from publicly available information on protein sequences,
2. calculating computationally the sequence based attributes of the protein sequences in the publicly available protein datasets using specially developed Software for Prediction of Adhesins and Adhesin-like proteins using Neural Networks (SPAAN),
3. training the Artificial Neural Network (ANN) for the selected attributes,
4. assigning probability value suitable for an adhesin, "$P_{ad}$" to the query protein and identifying adhesin like property in the query proteins with the help of trained Artificial Neural Network implemented in SPAAN,
5. validating computationally the protein sequences as therapeutic potentials by comparing with the known protein sequences that are biochemically characterized in the pathogen genome.

In an embodiment of the invention the protein sequence data may be taken from an organism, specifically but not limited to organisms such as *Escherichia coli, Haemophilus influenzae, Helicobacter pylori, Mycoplasma pneumoniae, Mycobacterium tuberculosis, Rickettsiae prowazekii, Porphyromonas gingivalis, Shigella flexneri, Streptococcus mutans, Streptococcus pneumoniae, Neisseria meningitides, Streptococcus pyogenes, Treponema pallidum,* Severe Acute Respiratory Syndrome associated coronavirus.

In another embodiment to the present invention different sequence-based attributes used for identification of proteins of therapeutic potential, comprise amino acid composition, charge composition, hydrophobicity composition, multiplets frequencies, and dipeptide frequencies.

In an embodiment, the non-homologous adhesin protein sequence may be compared with that of known sequences of therapeutic applications in the selected pathogens.

In an embodiment of the invention, the sequences of adhesin or adhesin like proteins comprise sequences of sequences IDs listed in Tables 5 and.6 identified by the method of invention.

Another embodiment of the invention the computer system comprises a central processing unit, executing SPAAN program, giving probabilities based on different attributes using Artificial Neural Network and in built other programs of assessing attributes, all stored in a memory device accessed by CPU, a display on which the central processing unit displays the screens of the above mentioned programs in response to user inputs; and a user interface device.

In One embodiment of the present invention, the particulars of the organisms such as their name, strain, accession number in NCBI database and other details are given in Table 2:

The invention is further explained with the help of the following examples, which are given by illustration and should be construed to limit the scope of the present invention in any manner.

EXAMPLE 1

Operating SPAAN:

The purpose of the program is to computationally calculate various sequence-based attributes of the protein sequences.

The program works as follows:

The internet downloaded FASTA format files obtained from http://www.ncbi.nlm.nih.gov were saved by the name <organism_name>.faa are converted in the standard format by C program and passed as input to another set of C programs which computes the 5 different attributes of protein sequences (a total of 105 compositional properties in all 5 modules).

The computed properties were fed as input to the 5 different Neural Networks. Each trained network assigns a probability value of being an adhesin for a query protein. The final probability ($P_{ad}$) was calculated as weighted average of these five individual probabilities. The weights were determined from a correlation value of correct; prediction during test runs of each of the five modules.

Input/Output format:

Downloaded Files and their format:

<organism name>.faa: file which stores the annotation and the protein sequence.

Input file Format: FASTA

">gi.vertline."<annotation>

For example,

>gi.vertline.2314605.vertline.gb.vertline.AAD08472.vertline.histidine and glutamine-rich protein

MAHHEQQQQQQANSQHHHHHHHAHHHHYYGGEHHHHHNAQQHAEQQAEQQ

AQQQQQQQAHQQQQQKAQQQNQQY

>gi.vertline.3261822.vertline.gnl.vertline.PID.vertline.e328405 PE_PGRS

MIGDGANGGPGQPGGPGGLLYGNGGHGGAGAAGQDRGAGNSAGLIGNGGA

GGAGGNGGIGGAGAPGGLGGDGGKGGFADEFTGGFAQGGRGGFGGNGNTG

ASGGMGGAGGAGGAGGAGGLLIGDGGAGGAGGIGGAGGVGGGGGAGGTGG

GGVASAFGGGNAFGGRGDGGDGGDGGTGGAGGARGAGGAGGAGGWLSGH

SGAHGAMGSGGEGGAGGGGARGEAGAGGGTSTGTNPGKAGAPGTQGDSG

DPGPPG

>gi.vertline. . . . .

TABLE 1

| | Output file format given by SPAAN <organism_name>.out | | | | | | |
|---|---|---|---|---|---|---|---|
| SN | $P_A$ | $P_C$ | $P_D$ | $P_H$ | $P_M$ | $P_{ad}$-value | Protein Name |
| 1 | 0.05683 | 0.290803 | 0.441338 | 0.50304 | 0.029503 | 0.260485 | >gi.vertline.32454344.vertline.gb.vertline.AAP82966.1.vertline.orf1a polyprotein [SARS coronavirus Hong Kong ZY-2003] |
| 2 | 0.639235 | 0.166721 | 0.054583 | 0.935385 | 0.453498 | 0.462452 | >gi.vertline.32454345.vertline.gb.vertline.AAP82967.1.vertline.orf1ab polyprotein [SARS coronavirus Hong Kong ZY-2003] |
| 3 | 0.651111 | 0.911504 | 0.438696 | 0.543944 | 0.924044 | 0.690247 | >gi.vertline.32454346.vertline.gb.vertline.AAP82968.1.vertline.spike glycoprotein [SARS coronavirus Hong Kong ZY-2003] |

TABLE 1-continued

Output file format given by SPAAN
<organism_name>.out

| SN | $P_A$ | $P_C$ | $P_D$ | $P_H$ | $P_M$ | $P_{ad}$-value | Protein Name |
|---|---|---|---|---|---|---|---|
| 4 | 0.464324 | 0.655003 | 0.179503 | 0.008700 | 0.241573 | 0.300970 | >gi.vertline.32454347.vertline.gb.vertline.AAP82969.1.vertline.Orf3a [SARS coronavirus Hong Kong ZY-2003] |

Where $P_A$, $P_C$, $P_D$, $P_H$, $P_M$ are the outputs of the five Neural Networks.

EXAMPLE 2

Organisms and Sequence Numbers

TABLE 2

Organism Name, Accession number, Number of base pairs, Date of release and Total number of proteins analyzed

| Organism Name | Accession Number | Number of base pairs | Date of release | Total no. of proteins |
|---|---|---|---|---|
| E. coli O157 H7 | NC_002695 | 5498450 | 7 Mar. 2001 | 5361 |
| H. influenzae Rd | NC_000907 | 1830138 | 30 Sep. 1996 | 1709 |
| H. pylori J99 | NC_000921 | 1643831 | 10 Sep. 2001 | 1491 |
| M. pneumoniae | NC_000912 | 816394 | 2 Apr. 2001 | 689 |
| M. tuberculosis H37Rv | NC_000962 | 4411529 | 7 Sep. 2001 | 3927 |
| R. prowazekii strain Madrid E | NC_000963 | 1111523 | 10 Sep. 2001 | 835 |
| P. gingivalis W83 | NC_002950 | 2343476 | 9 Sep. 2003 | 1909 |
| S. flexneri 2a str. 2457T | NC_004741 | 4599354 | 23 Apr. 2003 | 4072 |
| S. mutans UA159 | NC_004350 | 2030921 | 25 Oct. 2002 | 1960 |
| S. pneumoniae R6 | NC_003098 | 2038615 | 6 Sep. 2001 | 2043 |
| N. meningitidis serogroup A strain Z2491 | NC_003116 | 2184406 | 27 Sep. 2001 | 2065 |
| S. pyogenes MGAS8232 | NC_003485 | 1895017 | Jan. 31, 2002 | 1845 |
| T. pallidum subsp. pallidum str. Nichols | NC_000919 | 1138011 | 7 Sep. 2001 | 1036 |
| Severe Acute Respiratory Syndrome (SARS) associated coronavirus Frankfurt 1 | AY291315 | 29727 | 11 JUN. 2003 | 14 |
| SARS coronavirus HSR1 | AY323977 | 29751 | 15 OCT. 2003 | 14 |
| SARS coronavirus ZJ01 | AY297028 | 29715 | 19 MAY 2003 | 3 |
| SARS coronavirus TW1 | AY291451 | 29729 | 14 MAY 2003 | 11 |
| SARS coronavirus CUHK-Su10 | AY282752 | 29736 | 07 MAY 2003 | 4 |
| SARS coronavirus Urbani | AY278741 | 29727 | 12 AUG. 2003 | 12 |
| SARS coronavirus | NC_004718 | 29751 | 9 Sep. 2003 | 29 |
| SARS coronavirus Tor2 | AY274119 | 29751 | 16 MAY 2003 | 15 |
| SARS coronavirus GD01 | AY278489 | 29757 | 18 AUG. 2003 | 12 |
| SARS coronavirus CUHK-W1 | AY278554 | 29736 | 31 JUL. 2003 | 11 |
| SARS coronavirus BJ01 | AY278488 | 29725 | 01 MAY 2003 | 11 |

EXAMPLE 3

The multi-layered feed forward Neural Network architecture implemented in SPAAN (FIG. 1). A given protein sequence in FASTA format is first processed through the 5 modules A, C, D, H, and M to quantify the five types of compositional attributes. A: Amino acid composition, C: Charge composition, D: dipeptide composition of the 20 dipeptides (NG, RE, TN, NT, GT, TT, DE, ER, RR, RK, RI, AT, TS, IV, SG, GS, TG, GN, VI, HR), H: Hydrophobic composition, M: Amino acid frequencies as Multiplets. The sequence shown is part of the FimH precursor (gi 5524634) of E. coli. Subsequently, these numerical data are input to the input neuron layer. The directions of arrows show data flow. The number of neurons chosen in the input layer was equal to the number of the numerical input vectors of each module. The network was optimally trained through minimization of error of detection based on validate set through back propagation. The details are described in the methods. Each network module assigns a probability value of the protein being an adhesin based on the corresponding attribute. The final probability of a protein sequence being an adhesin is the $P_{ad}$ value a weighted average of the individual probabilities and the associated fraction of correlation which is a measure of the strength of the prediction.

EXAMPLE 4

Performance of SPAAN assessed using a test set of 37 adhesins and 37 non-adhesins that were not part of the training set. Matthew's correlation coefficient (Mcc, plotted on Y-axis) for all the proteins with $P_{ad}$ values above a given threshold (plotted on X-axis) (FIG. 2). The Matthew's correlation is defined as:

$$Mcc = \frac{(TP*TN) - (FP*FN)}{\sqrt{(TN+FN)(TN+FP)(TP+FN)(TP+FP)}}$$

Where TP=True Positives, TN=True Negatives, FP=False Positives, FN=False Negatives.

Here TPs are adhesins, TNs are non-adhesins. In general, adhesins have high $P_{ad}$ value, whereas non-adhesins have low $P_{ad}$ value. Thus known adhesins with $P_{ad}$ value above a given threshold are true positives whereas known non-adhesins with $P_{ad}$ value below the given threshold are true negatives. The sensitivity, Sn is given by $$\left(\frac{TP}{TP+FN}\right)$$

and specificity, Sp is given by $$\left(\frac{TP}{TP+FP}\right).$$

False negatives are those cases, wherein a known adhesin had $P_{ad}$ value lower than the chosen threshold. Similarly, a known non-adhesin with a $P_{ad}$ value higher than the chosen threshold was taken as false positive. A theoretical polynomial curve of second order (dashed line) was fitted to the observed curve (smooth line) with a Karl-Pearson correlation coefficient $R^2=0.9799$. The maximum point of the theoretical curve (where first derivative vanishes and second derivative is negative) was chosen as reference (vertical dotted line) to identify the maximum Mcc=0.94 on the observed curve (shown by arrow). The corresponding $P_{ad}$ value threshold was 0.51. At this $P_{ad}$ value threshold, Sn and Sp were 0.89 and 1.0 respectively. Note that the Mcc does not drop down to the x-axis because the highest $P_{ad}$ value attained by adhesins was 0.939 in comparison to the theoretical attainable limit of 1.0.

EXAMPLE 5

Assessment of SPAAN on well known adhesins from various bacterial pathogens.

TABLE 3

Prediction of well characterized adhesins from various bacterial pathogens using SPAAN.

| Species | Disease caused | Adhesin[a] | Host ligand | $P_{ad}$ value[b] (Range) |
|---|---|---|---|---|
| E. coli | Diarrhoea | PapG (27) | α-D-gal(1-4) β-D-Gal-containing receptors | 0.84-0.76 |
| | | SfaS (5) | alpha-sialyl-beta-2,3-b-galactose | 0.94-0.94 |
| | | FimH (63) | D-mannosides | 0.96-0.23[c] |
| | | Intimin (12) | tyrosine-phosphorylated form of host cell receptor Hp90 | 0.95-0.78 |
| | | PrsG (5) | Gal(alpha1-4)Gal | 0.86-0.85 |
| Nontypeable H. influenza | Influenza | HMW1, HMW2 | Human epithelial cells | 0.97 |
| | | Hia (8) | human conjuctival cells | 0.93-0.90 |
| H. influenzae | bacterial meningitis[d] | HifE (18) | Sialylyganglioside-GM1 | 0.85-0.73 |
| K. pneumoniae | Pneumonia | MrkD | type V collagen | 0.82 |
| B. pertussis | Whooping cough | FHA | Sulphated sugars on cell-surface glycoconjugates | 0.85 |
| | | Pertactin | Integrins | 0.43 |
| Y. enterocolitica | Enterocolitis | YadA (5) | $\beta_1$ integrins | 0.88-0.79 |
| S. mutans | Dental Caries | SpaP (2) | Salivary glycoprotein | 0.88, 0.87 |
| | | PAc | Salivary glycoprotein | 0.88 |
| Streptococcus gordonii | Oral cavity | SspA (2) | Salivary glycoprotein | 0.85, 0.84 |
| | | CshA | Fibronectin | 0.78 |
| | | CshB | Fibronectin | 0.63 |
| | | ScaA | Co-aggregation | 0.71 |
| | | SspB (2) | Salivary glycoprotein | 0.85, 0.84 |
| Streptococcus sobrinus | Tooth decay | SpaA | Salivary glycoprotein | 0.89 |
| | | PAg (2) | Salivary glycoprotein | 0.89, 0.73 |
| Streptococcus pyogenes | Scarlet Fever | Protein F | Fibronectin | 0.49 |
| Streptococcus pneumoniae | Bacterial Pneumonia | PsaA (5) | Human nasopharyngeal cells | 0.82-0.78 |
| | | CbpA[e]/ SpsA/ PbcA/PspC | phosphorylcholine of the teichoic acid. | 0.81-0.49 |
| Streptococcus parasanguis | Valve endocarditis | FimA | Salivary glycoprotein fibrin | 0.76 |
| Streptococcus sanguis | Tooth Decay | SsaB | Salivary glycoprotein | 0.71 |
| Enterococcus | Empyma in | EfaA | Unknown | 0.83 |

TABLE 3-continued

Prediction of well characterized adhesins from various bacterial pathogens using SPAAN.

| Species | Disease caused | Adhesin[a] | Host ligand | $P_{ad}$ value[b] (Range) |
|---|---|---|---|---|
| faecalis | patients with liver disease | | | |
| Staphylococcus aureus | Food Poisoning | FnbA FnbB (3) | Fibronectin Fibronectin | 0.8 0.78, 0.77, 0.69 |
| Helicobacter pylori | Peptic Ulcers | BabA (17) | difucosylated Lewis[b] blood group antigen | 0.87-0.68 |

[a]The number of sequences from different strains and homologs from related species analyzed are shown in parantheses.
[b]Rounded off to the second decimal.
[c]Out of 63 FimH proteins, 54 were from *E. coli*, 6 from *Shigella flexineri*, 2 from *Salmonella enterica* and 1 was from *Salmonella typhimurium*. Except 2 FimH proteins, the rest had $P_{ad} \geq 0.51$. The 2 exceptions (gi numbers: 5524636, 1778448) were from *E. coli*. The gi: 5524636 protein is annotated as a FimH precursor but is much shorter (129 amino acids) than other members of the family. The gi: 1778448 protein is a *S. typhimurium* homolog in *E. coli*.
[d]Other ailments include pneumonia, epiglottitis, osteomyelitis, septic arthritis and sepsis in infants and older children.
[e]The adhesin CbpA is also known by alternative names SpsA, PbcA and PspC. A total of seven sequences were analyzed. Except 1 PspC sequence, the rest all had $P_{ad} \geq 0.51$.

EXAMPLE 6

Ability of SPAAN to discriminate adhesins from non-adhesins at $P_{ad} \geq 0.51$ (FIG. 3-*a*).

EXAMPLE 7

Figure 3C:
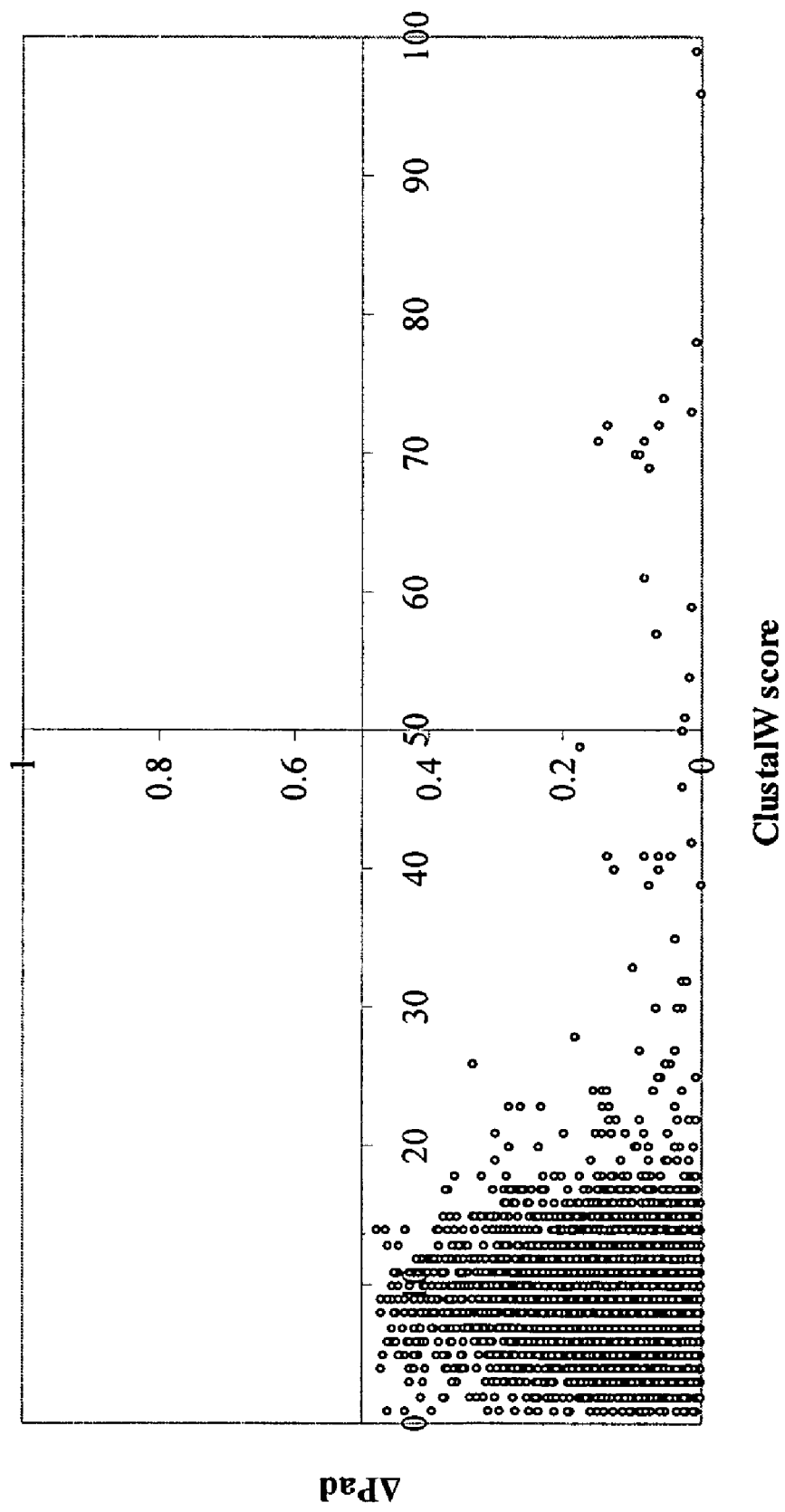

The non-homology character of SPAAN assesses in both adhesins and non-adhesins (FIGS. 3*b* and 3*c*).

FIG. 3(*a-c*). SPAAN is non-homology based software. A total of 130 adhesins and 130 non-adhesins were analyzed to assess whether the predictive power of SPAAN could be influenced by the sequence relationships. (a) Histogram plots of the number of proteins in the various $P_{ad}$ value ranges are shown. Shaded bars represent adhesins whereas open bars represent non-adhesins. Note the SPAAN's ability to segregate adhesins and non-adhesins into two distinct cohesive groups. (b) Pairwise sequence relationships among the adhesins were determined using CLUSTAL W and plotted on X-axis. Higher scores indicate similar pairs. The corresponding differences in $P_{ad}$ values in the same protein pair was plotted on the Y-axis. Each point in the diagram represents a pair. Arrow points to protein pairs of the FimH family with high $\Delta P_{ad}$ values in spite of high similarity. Since one of the FimH proteins (gi: 5524636) had very low $P_{ad}$ value all pairs with this false negative protein show high $\Delta P_{ad}$ values. The protein (gi: 5524636) is of much shorter length compared with other members of the same family. (c) plot for non-adhesins. Data are plotted in the 4 quadrant format for clear inspection. Note that among protein pairs with CLUSTAL W score <20 the majority (82% in adhesins and 86% in non-adhesins) have $\Delta P_{ad} < 0.2$. These data support the non-homology character of SPAAN.

EXAMPLE 8

Genomescan of pathogens by SPAAN identifies well known adhesins and new adhesins and adhesin-like proteins

TABLE 4

Analysis of predictions made by SPAAN on genome scans of a few selected pathogenic organisms[a]

| Protein Class | Species | | |
|---|---|---|---|
| | *Escherichia coli* O157:H7 | *Mycobacterium tuberculosis* H37Rv | SARS associated corona virus (11 strains) |
| Total number of proteins with $P_{ad} \geq 0.51$ | 575 | 435 | 5 |
| Known adhesins | 17[b] | — | — |
| Putative proteins with adhesin like characteristics | 92[c] | 105[j] | — |
| Hypothetical proteins with adhesin-like characteristics | 22[d] | — | — |
| Proteins likely to be extracytoplasmic or located at surface | 190[e] | 191[k] | 5[m] |
| Phage proteins | 30[f] | — | — |
| Others | 13[g] | 6[l] | — |
| Hypothetical proteins | 157[h] | 86[h] | — |
| Wrong predictions | 54[i] | 47[i] | — |

[a]SPAAN has general applicability. The three pathogens chosen here are those in which intense investigations are being conducted presently. *M. tuberculosis* is of special importance to developing countries.
[b]Fimbrial adhesins, AidA-I, gamma intimin, curlin, translocated intimin receptor, putative adhesin and transport, Iha, prepilin peptidase dependent protein C.
[c]These proteins have been annotated as proteins with a putative function. These sequences were analyzed using CDD (Conserved domain database, NCBI) and BLAST searches. Adhesin like domains were found in these proteins.
[d]These proteins have been annotated as 'hypothetical'. These sequences were analyzed using CDD and BLAST searches. Adhesin like domains were found in these proteins.
[e]These proteins are outer membrane, extracellular, transport, surface, exported, flagellar, periplasmic lipoprotein, and proteins annotated as 'hypothetical' but found to have similar functions listed here using BLAST and CDD searches.
[f]The phage proteins were of the following functional roles - tail fiber, head decoration, DNA injection, tail, major capsid, host specificity, endolysin.

TABLE 4-continued

Analysis of predictions made by SPAAN on genome scans of a few selected pathogenic organisms[a]

| Protein Class | Species | | |
|---|---|---|---|
| | *Escherichia coli* O157:H7 | *Mycobacterium tuberculosis* H37Rv | SARS associated corona virus (11 strains) |

[g]Proteins predicted by SPAAN but not readily classifiable into the classes listed here have been collectively grouped as 'Others'. However, some of these proteins are known to participate in host-pathogen interactions. The annotated functional roles are typeIII secretion, antibiotic resistance, heat shock, acid shock, structural, tellurium resistance, terminase, Hcp-like, Sec-independent translocase, uncharacterized nucleoprotein, HicB-like.
[h]These proteins have been annotated as hypothetical. Re-analyses of these proteins using BLAST and CDD failed identify any function for these proteins.
[i]These proteins have been annotated with functional roles that are very likely to occur within the cell. Hence these proteins may have remote possibility of functioning as adhesins or adhesin-like proteins. Therefore this set of proteins have been incorrectly predicted as adhesins or adhesin-like by SPAAN.
[j]These proteins are PE_PGRS, PE proteins. Several reports (for example Brennan et al.) indicate that PE_PGRS proteins may be localized to cell surface and aid in host-pathogen interaction.
[k]Lipoproteins (lpp, lpq, lpr), PPE, outer membrane, surface, transport, secreted, periplasmic, extracellular, ESAT-6, peptidoglycan binding, exported, mpt (with extracellular domains), and proteins annotated as 'hypothetical' but found to have similar functions listed here using BLAST and CDD searches.
[l]These proteins were of the following functions - glutaredoxin-like thiol-transferase, putative involvement in molybdate uptake, ATP synthase chain, sulphotransferases, *S. erythraea* rhodanese-like protein M29612|SERCYSA_5, unknown function.
[m]These proteins were the spike glycoprotein with antigenic properties, and nsp2, nsp5, nsp6 and nsp7.

TABLE 5

New putative adhesins predicted by SPAAN in the genomes listed in table 2 -
(Total number = 279)

| Protein GI Number | Gene ID | Protein name |
|---|---|---|
| | | *Escherichia coli* O157:H7 |
| 13360742 | 912619 | hemagglutinin/hemolysin-related protein |
| 13362986 | 914770 | putative ATP-binding component of a transport system |
| 13361114 | 913228 | putative tail fiber protein |
| 13364757 | 913676 | minor fimbrial subunit/D-mannose specific adhesin |
| 13362687 | 915687 | putative fimbrial-like protein |
| 13360856 | 912599 | AidA-I adhesin-like protein |
| 13364140 | 915374 | putative fimbrial protein |
| 13359793 | 914435 | putative invasin |
| 13364768 | 913650 | putative invasin |
| 13364034 | 915471 | Gamma intimin |
| 13362703 | 915668 | putative DNA transfer protein precursor |
| 13364141 | 915376 | putative fimbrial protein |
| 13359819 | 914463 | AidA-I adhesin-like protein |
| 13360480 | 917768 | putative fimbrial-like protein |
| 13362692 | 915681 | putative fimbrial-like protein |
| 13362585 | 916824 | putative ATP-binding component of a transport system |
| 13359881 | 914526 | putative flagellin structural protein |
| 13361579 | 917311 | putative type 1 fimbrial protein precursor |
| 13360880 | 913991 | curlin major subunit CsgA |
| 13364036 | 915465 | translocated intimin receptor Tir |
| 13360740 | 912615 | putative major pilin protein |
| 13361582 | 917317 | putative ATP-binding component of a transport system and adhesin protein |
| 13364754 | 913683 | export and assembly outer membrane protein of type 1 fimbriae |
| 13360484 | 917767 | homolog of *Salmonella* FimH protein |
| 13364751 | 913688 | major type 1 subunit fimbrin |
| 13359597 | 913742 | putative fimbrial protein |
| 13362550 | 916787 | putative ATP-binding component of a transport system |
| 13359595 | 913739 | putative fimbrial protein |
| 13359599 | 913748 | probable outer membrane porin protein involved in fimbrial assembly |
| 13363900 | 915704 | putative fimbrial protein precursor |
| 13361575 | 917307 | putative fimbrial-like protein |
| 13364756 | 913678 | fimbrial morphology |
| 13363496 | 916142 | truncated putative fimbrial protein |
| 13359601 | 913761 | putative fimbrial-like protein |
| 13364145 | 915368 | putative type 1 fimbrial protein |
| 13363902 | 915708 | putative outer membrane usher protein precursor |
| 13361576 | 917309 | putative outer membrane protein |
| 13361013 | 913353 | putative major tail subunit |
| 13364755 | 913682 | fimbrial morphology |

TABLE 5-continued

New putative adhesins predicted by SPAAN in the genomes listed in table 2 -
(Total number = 279)

| Protein GI Number | Gene ID | Protein name |
|---|---|---|
| 13360738 | 912793 | putative outer membrane usher protein |
| 13363928 | 915608 | alpha-amylase |
| 13363495 | 916144 | putative outer membrane protein |
| 13362383 | 916617 | putative type-1 fimbrial protein |
| 13364373 | 914972 | outer membrane vitamin B12 receptor protein BtuB |
| 13360879 | 912479 | minor curlin subunit precursor CsgB |
| 13360739 | 912756 | putative chaperone protein |
| 13361574 | 917314 | putative fimbrial-like protein |
| 13361127 | 913212 | outer membrane protease precursor |
| 13363210 | 916442 | putative lipoprotein |
| 13361104 | 913238 | major tail protein |
| 13361709 | 917446 | putative major tail subunit |
| 13359725 | 914366 | outer membrane pore protein PhoE |
| 13360875 | 913765 | curli production assembly/transport component CsgF |
| 13362170 | 913927 | putative outer membrane protein |
| 13361473 | 917203 | putative BigB-like protein |
| 13364025 | 915286 | EspF protein |
| 13360081 | 916982 | outer membrane receptor for ferric enterobactin (enterochelin) and colicins B and D |
| 13362977 | 914779 | hypothetical lipoprotein |
| 13360351 | 917632 | outer membrane protein X |
| 13360696 | 914208 | putative outer membrane precursor |
| 13361456 | 917206 | putative outer membrane protein |
| 13361626 | 917374 | putative outer host membrane protein precursor |
| 13361698 | 917449 | putative outer membrane protein |
| 13362186 | 913421 | putative outer membrane protein precursor |
| 13362697 | 915676 | long-chain fatty acid transport protein FadL |
| 13360918 | 914188 | flagellar hook protein FlgE |
| 13360737 | 912506 | putative outer membrane protein |
| 13360342 | 917629 | putative outer membrane receptor for iron transport |
| 13363396 | 916248 | outer membrane channel TolC |
| 13361958 | 912705 | putative scaffolding protein in the formation of a murein-synthesizing holoenzyme |
| 13359921 | 914566 | nucleoside-specific channel-forming protein TSX |
| 13360944 | 913890 | outer membrane receptor for ferric iron uptake |
| 13359998 | 914644 | putative outer membrane transport protein |
| 13363390 | 916251 | putative ferrichrome iron receptor precursor |
| 13364227 | 915153 | outer membrane phospholipase A |
| 13361982 | 912846 | putative outer membrane protein |
| 13360129 | 917032 | a minor lipoprotein |
| 13361817 | 912692 | putative outer membrane protein |
| 13360233 | 917507 | membrane spanning protein TolA |
| 13362837 | 915218 | putative outer membrane lipoprotein |
| 13362328 | 912985 | putative colanic acid biosynthesis glycosyl transferase |
| *Haemophilus influenzae* Rd | | |
| 16272254 | 949521 | prepilin peptidase-dependent protein D |
| 16272928 | 950762 | immunoglobin A1 protease |
| 16272129 | 951072 | lipoprotein |
| 16273251 | 950616 | hemoglobin-binding protein |
| 30995429 | 950130 | opacity protein |
| 16272854 | 949634 | protective surface antigen D15 |
| 16272283 | 950648 | opacity associated protein |
| 16272604 | 949701 | hemoglobin-binding protein |
| *Helicobacter pylori* J99 | | |
| 4155101 | 889167 | putative vacuolating cytotoxin (VacA) paralog |
| 4154798 | 890022 | putative vacuolating cytotoxin (VacA) paralog |
| 4155426 | 890036 | putative vacuolating cytotoxin (VacA) paralog |
| 4155390 | 890075 | vacuolating cytotoxin |
| 4155400 | 890058 | outer membrane protein - adhesin |
| 4155681 | 889718 | putative Outer membrane protein |
| 4155420 | 890042 | Outer membrane protein/porin |
| 4155775 | 889799 | outer membrane protein - adhesin |
| 4155419 | 890044 | Outer membrane protein/porin |
| 4154526 | 889066 | putative Outer membrane protein |
| 4154724 | 889419 | putative Outer membrane protein |
| 4155862 | 890404 | putative Outer membrane protein |
| 4156048 | 889958 | putative IRON(III) DICITRATE TRANSPORT PROTEIN |
| 4154510 | 889297 | putative Outer membrane protein |
| 4155432 | 889515 | putative outer membrane protein |
| 4155623 | 889671 | putative Outer membrane protein |

TABLE 5-continued

New putative adhesins predicted by SPAAN in the genomes listed in table 2 -
(Total number = 279)

| Protein GI Number | Gene ID | Protein name |
|---|---|---|
| 4155700 | 889739 | putative Outer membrane function |
| 4154740 | 889426 | Outer membrane protein/porin |
| 4155692 | 889743 | putative Outer membrane protein |
| 4155594 | 889648 | putative outer membrane protein |
| 4155680 | 889719 | putative Outer membrane protein |
| 4155217 | 890243 | putative Outer membrane protein |
| 4155958 | 889905 | putative Outer membrane protein |
| 4155201 | 890259 | putative Outer membrane protein |
| 4155013 | 889232 | cag island protein |
| 4154974 | 889032 | putative Outer membrane protein |
| 4155214 | 890244 | putative Outer membrane protein |
| 4154973 | 889042 | Outer membrane protein |
| 4155344 | 890115 | putative Outer membrane protein |
| 4155099 | 889160 | FLAGELLIN A |
| 4155023 | 888978 | cag island protein |
| 4155035 | 889201 | cag island protein, CYTOTOXICITY ASSOCIATED IMMUNODOMINANT ANTIGEN |
| 4155289 | 890164 | NEURAMINYLLACTOSE-BINDING HEMAGGLUTININ PRECURSOR |

*Mycoplasma pneumoniae*

| | | |
|---|---|---|
| 13507881 | 877207 | involved in cytadherence |
| 13507880 | 877268 | ADP1_MYCPN adhesin P1 |
| 13508228 | 877211 | species specific lipoprotein |
| 13508181 | 877124 | species specific lipoprotein |
| 13508179 | 877071 | Mollicute specific lipoprotein, MG307 homolog, from *M. genitalium* |
| 13508178 | 877118 | Mollicute specific lipoprotein, MG307 homolog, from *M. genitalium*, |
| 13508176 | 876797 | Mollicute specific lipoprotein, MG307 homolog, from *M. genitalium* |
| 13508175 | 876848 | Mollicute specific lipoprotein, MG307 homolog, from *M. genitalium* |
| 13508106 | 876953 | involved in cytadherence |
| 13508350 | 877112 | similar to phosphate binding protein Psts |

*Mycobacterium tuberculosis* H37 Rv

| | | |
|---|---|---|
| 15607496 | 886491 | PPE |
| 15607445 | 886592 | PPE |
| 15610644 | 888270 | PE_PGRS |
| 15608588 | 886605 | PE_PGRS |
| 15609627 | 887941 | PE_PGRS |
| 15610643 | 888256 | PE_PGRS |
| 15607718 | 887725 | PE_PGRS |
| 15609054 | 885362 | PPE |
| 15610486 | 888113 | PPE |
| 15610483 | 888120 | PPE |
| 15610479 | 888033 | PPE |
| 15609771 | 888573 | PE_PGRS |
| 15610648 | 888306 | PE_PGRS |
| 15610481 | 888114 | PE_PGRS |
| 15608117 | 885264 | PE_PGRS |
| 15607973 | 885391 | PE_PGRS |
| 15608231 | 885258 | PE_PGRS |
| 15608906 | 885429 | PE_PGRS |
| 15608891 | 885544 | PPE |
| 15609990 | 888171 | PE_PGRS |
| 15609055 | 885506 | PPE |
| 15608227 | 887094 | PE_PGRS |
| 15610524 | 888151 | PE_PGRS |
| 15609490 | 886003 | PPE |
| 15607886 | 888664 | PE_PGRS |
| 15609624 | 887909 | PE_PGRS |
| 15607420 | 886621 | PE_PGRS |
| 15608897 | 885325 | PE_PGRS(wag22) |
| 15608590 | 886595 | PE_PGRS |
| 15609728 | 887992 | PE_PGRS |
| 15608012 | 885742 | PE_PGRS |
| 15608534 | 886745 | PE_PGRS |
| 15608940 | 885730 | PE_PGRS |
| 15607887 | 888662 | PE_PGRS |
| 15609235 | 888312 | PE_PGRS |
| 15610694 | 887822 | PPE |
| 15609533 | 885517 | PE_PGRS |
| 15610480 | | PE_PGRS |

TABLE 5-continued

New putative adhesins predicted by SPAAN in the genomes listed in table 2 - 
(Total number = 279)

| Protein GI Number | Gene ID | Protein name |
|---|---|---|
| \multicolumn{3}{c}{*Rickettsia prowazekii* strain Madrid E} |
| 15604316 | 883411 | CELL SURFACE ANTIGEN (sca3) |
| 15604546 | 883694 | CELL SURFACE ANTIGEN (sca5) |
| \multicolumn{3}{c}{*Porphyromonas gingivalis* W83} |
| 34541453 | 2551934 | hemagglutinin protein HagA |
| 34540040 | 2551409 | lipoprotein, putative |
| 34540364 | 2552375 | extracellular protease, putative |
| 34541613 | 2552074 | hemagglutinin protein HagE |
| 34540183 | 2551891 | internalin-related protein |
| \multicolumn{3}{c}{*Shigella flexneri* 2a str. 2457T} |
| 30065424 | 1080663 | minor fimbrial subunit, D-mannose specific adhesin |
| 30062726 | 1077662 | putative adhesion and penetration protein |
| 30063758 | 1078834 | putative fimbrial-like protein |
| 30065431 | 1080671 | major type 1 subunit fimbrin (pilin) |
| 30063366 | 1078379 | flagellar protein FliD |
| 30064308 | 1079668 | outer membrane fluffing protein |
| 30062613 | 1077555 | flagellar hook protein FlgE |
| 30061954 | 1076843 | conserved hypothetical lipoprotein |
| 30065173 | 1080393 | putative lipase |
| 30065425 | 1080664 | minor fimbrial subunit, precursor polypeptide |
| 30064485 | 1079637 | putative fimbrial protein |
| 30062615 | 1077558 | flagellar basal body L-ring protein FlgH |
| 30064307 | 1079452 | outer membrane fluffing protein |
| 30065601 | 1080859 | putative glycoprotein/receptor |
| 30062118 | 1077025 | putative fimbrial-like protein |
| 30064099 | 1079223 | lipoprotein |
| 30062616 | 1077559 | flagellar basal body P-ring protein FlgI |
| 30063546 | 1078596 | putative fimbrial-like protein |
| 30062940 | 1077910 | putative outer membrane protein |
| 30065426 | 1080665 | minor fimbrial subunit, precursor polypeptide |
| 30062779 | 1077721 | putative outer membrane protein |
| 30064194 | 1079329 | putative lipoprotein |
| 30063365 | 1078378 | flagellin |
| 30062298 | 1077222 | outer membrane protein X |
| 30064968 | 1080175 | putative major fimbrial subunit |
| 30061858 | 1076740 | outer membrane pore protein E (E, Ic, NmpAB) |
| 30062178 | 1080410 | minor lipoprotein |
| 30062479 | 1077412 | putative fimbrial-like protein |
| 30062565 | 1077506 | minor curlin subunit precursor |
| 30063880 | 1078972 | putative outer membrane lipoprotein |
| 30064531 | 1079686 | cytoplasmic membrane protein |
| 30065033 | 1080243 | putative receptor protein |
| \multicolumn{3}{c}{*Streptococcus mutans* UA159} |
| 24378550 | 1029610 | putative secreted antigen GbpB/SagA; putative peptidoglycan hydrolase |
| 24379087 | 1028055 | cell surface antigen SpaP |
| 24380463 | 1029310 | putative membrane protein |
| 24379075 | 1028046 | penicillin-binding protein 2b |
| 24378955 | 1027967 | penicillin-binding protein 1a; membrane carboxypeptidase |
| 24379801 | 1028662 | glucan-binding protein C, GbpC |
| 24379528 | 1029536 | hypothetical protein; possible cell wall protein, WapE |
| 24379231 | 1028158 | putative glucan-binding protein D; BglB-like protein |
| 24380488 | 1029325 | conserved hypothetical protein; possible transmembrane protein |
| 24380291 | 1029139 | putative amino acid binding protein |
| 24379342 | 1028247 | putative penicillin-binding protein, class C; fmt-like protein |
| 24380047 | 1028904 | putative ABC transporter, branched chain amino acid-binding protein |
| 24378698 | 1029755 | putative ABC transporter, metal binding lipoprotein; surface adhesin precursor; saliva-binding protein; lipoprotein receptor LraI (LraI family) |
| 24378708 | 1029768 | putative transfer protein |
| 24379427 | 1028331 | cell wall-associated protein precursor WapA |
| 24379272 | 1028196 | putative amino acid transporter, amino acid-binding protein |
| 24379641 | 1028511 | putative ABC transporter, amino acid binding protein |

TABLE 5-continued

New putative adhesins predicted by SPAAN in the genomes listed in table 2 -
(Total number = 279)

| Protein GI Number | Gene ID | Protein name |
|---|---|---|
| *Streptococcus pneumoniae* R6 | | |
| 15902395 | 934801 | Choline-binding protein |
| 15902381 | 934810 | Choline-binding protein F |
| 15902165 | 932894 | Surface protein pspA precursor |
| 15904047 | 934859 | Choline binding protein D |
| 15904036 | 933487 | Choline binding protein A |
| 15903986 | 933069 | Choline-binding protein |
| 15903796 | 933669 | Autolysin (N-acetylmuramoyl-L-alanine amidase) |
| *Neisseria meningitidis* Z2491 | | |
| 15794121 | 907145 | putative membrane protein |
| 15794144 | 907168 | putative surface fibril protein |
| 15793284 | 906275 | truncated pilin |
| 15793460 | 906456 | IgA-specific serine endopeptidase |
| 15793282 | 906273 | fimbrial protein precursor (pilin) |
| 15793337 | 906332 | adhesin |
| 15793253 | 906243 | putative lipoprotein |
| 15794356 | 907848 | putative lipoprotein |
| 15793684 | 906699 | putative membrane protein |
| 15793290 | 906281 | truncated pilin |
| 15793283 | 906274 | truncated pilin |
| 15793475 | 906471 | haemoglobin-haptoglobin-utilization protein |
| 15793406 | 906401 | porin, major outer membrane protein P.I |
| 15794985 | 907333 | adhesin MafA2 |
| 15794344 | 907836 | putative lipoprotein |
| 15794622 | 908118 | hypothetical outer membrane protein |
| 15793599 | 906604 | pilus-associated protein |
| 15793763 | 906779 | putative periplasmic binding protein |
| *Streptococcus pyogenes* MGAS8232 | | |
| 19745214 | 995235 | putative secreted protein |
| 19746570 | 994224 | putative penicillin-binding protein 1a |
| 19745593 | 994771 | putative 42 kDa protein |
| 19745813 | 993958 | putative adhesion protein |
| 19745225 | 994839 | putative choline binding protein |
| 19745828 | 995250 | streptolysin S associated protein |
| 19746229 | 995021 | putative minor tail protein |
| 19746909 | 994105 | putative laminin adhesion |
| 19745560 | 995061 | putative cell envelope proteinase |
| *Treponema pallidum* subsp. *pallidum* str. Nichols | | |
| 15639714 | 2611034 | flagellar hook protein (flgE) |
| 15639609 | 2611657 | tpr protein J (tprJ) |
| 15639111 | 2610909 | tpr protein C (tprC) |
| 15639125 | 2610968 | tpr protein D (tprD) |
| SARS coronavirus | | |
| 31581505 | | spike protein S [SARS coronavirus Frankfurt 1] |
| 32187357 | | spike protein S [SARS coronavirus HSR 1] |
| 32187342 | | spike glycoprotein [SARS coronavirus ZJ01] |
| 30698329 | | putative spike glycoprotein S [SARS coronavirus TW1] |
| 30421454 | | putative spike glycoprotein [SARS coronavirus CUHK-Su10] |
| 30027620 | | S protein [SARS coronavirus Urbani] |
| 29836496 | 1489668 | E2 glycoprotein precursor; putative spike glycoprotein [SARS coronavirus] |
| 30795145 | | spike glycoprotein [SARS coronavirus Tor2] |
| 31416295 | | spike glycoprotein S [SARS coronavirus GD01] |
| 30023954 | | putative E2 glycoprotein precursor [SARS coronavirus CUHK-W1] |
| 30275669 | | spike glycoprotein S [SARS coronavirus BJ01] |
| 29837498 | | 3C-like proteinase nsp5-pp1a/pp1ab (3CL-PRO) [SARS coronavirus] |
| 29837501 | | putative nsp8-pp1a/pp1ab [SARS coronavirus] |
| 29837503 | | putative nsp10-pp1a/pp1ab; formerly known as growth-factor-like protein [SARS coronavirus] |
| 29837502 | | putative nsp9-pp1a/pp1ab [SARS coronavirus] |

TABLE 6

Hypothetical proteins predicted as putative adhesins by SPAAN in the genomes listed in table 2 - (Total number of proteins = 105)

| Protein GI number | Gene ID |
|---|---|
| *Escherichia coli* O157:H7 | |
| 13363955 | 915578 |
| 13360000 | 914929 |
| 13362244 | 912369 |
| 13359999 | 914888 |
| 13361583 | 917316 |
| 13361172 | 913156 |
| 13361131 | 913207 |
| 13359780 | 914422 |
| 13360571 | 912499 |
| 13362197 | 912893 |
| 13362260 | 912399 |
| 13360947 | 913505 |
| 13361464 | 917196 |
| 13361635 | 917367 |
| 13362421 | 916655 |
| 13361463 | 917195 |
| *Haemophilus influenzae* Rd | |
| 16272115 | 951058 |
| 30995442 | 950581 |
| *Helicobacter pylori* J99 | |
| 4155526 | 889586 |
| 4155712 | 889748 |
| 4155632 | 889684 |
| 4156035 | 889468 |
| 4155499 | |
| *Mycoplasma pneumoniae* | |
| 13507870 | 877230 |
| 13508239 | 877245 |
| 13508109 | 876868 |
| 13508025 | 877084 |
| 13507838 | 876784 |
| 13507883 | 877183 |
| 13507871 | 877239 |
| 13507944 | 877056 |
| 13508241 | 876750 |
| 13507942 | 877055 |
| 13507840 | 877387 |
| 13507867 | 877242 |
| 13508201 | 877044 |
| 13507941 | 876985 |
| 13508114 | 877397 |
| *Mycobacterium tuberculosis* H37Rv | |
| 15611014 | 886198 |
| 15610173 | 887320 |
| 15609513 | 885515 |
| 15608094 | 885411 |
| 15610958 | 886155 |
| 15607528 | 886436 |
| 15607678 | 887473 |
| 15609587 | 885760 |
| 15610708 | 887227 |
| 15609526 | 885246 |
| 15611033 | 886225 |
| 15609028 | 885094 |
| 15607730 | 887771 |
| 15609121 | 885813 |
| 15608255 | 885951 |
| 15608409 | 887039 |
| 15609124 | 885815 |
| 15607734 | 887797 |
| *Rickettsia prowazekii* strain Madrid E | |
| 15604649 | 883964 |
| 15604322 | 883472 |
| 15604659 | 883996 |
| 15604417 | 883217 |

TABLE 6-continued

Hypothetical proteins predicted as putative adhesins by SPAAN in the genomes listed in table 2 - (Total number of proteins = 105)

| Protein GI number | Gene ID |
|---|---|
| *Porphyromonas gingivalis* W83 | |
| 34540233 | 2551594 |
| *Shigella flexneri* 2a str. 2457T | |
| 30062687 | 1077638 |
| 30062956 | 1080449 |
| 30063681 | 1078754 |
| 30065435 | 1080675 |
| 30063891 | 1078983 |
| 30063211 | 1078195 |
| 30065233 | 1080463 |
| 30064387 | 1079531 |
| 30062638 | 1077590 |
| 30065236 | 1080466 |
| 30061839 | 1076721 |
| *Streptococcus mutans* UA159 | |
| 24378864 | 1029452 |
| 24380475 | 1029319 |
| 24380237 | 1029088 |
| 24379203 | 1028139 |
| 24380480 | 1029320 |
| 24379275 | 1029489 |
| 24379291 | 1028216 |
| 24379295 | 1028215 |
| 24379804 | 1028663 |
| 24379162 | 1029417 |
| 24378987 | 1029363 |
| 24379179 | 1028118 |
| 24379166 | 1028107 |
| 24378827 | 1029444 |
| 24380216 | 1029067 |
| *Streptococcus pneumoniae* R6 | |
| 15902140 | 932867 |
| 15903446 | 934616 |
| 15903916 | 934001 |
| 15903848 | 933609 |
| 15902832 | 934332 |
| 15902372 | 934804 |
| 15902152 | 932889 |
| *Neisseria meningitidis* Z2491 | |
| 15793668 | 906680 |
| 15794714 | 907603 |
| *Streptococcus pyogenes* MGAS8232 | |
| 19747011 | 993608 |
| 19747024 | 994165 |
| 19747012 | 994373 |
| 19746396 | 995057 |
| 19746651 | 993824 |
| 19745883 | 995045 |
| 19745912 | 994077 |
| *Treponema pallidum* subsp. *pallidum* str. Nichols | |
| 15639844 | 2611061 |
| 15639720 | 2611059 |

TABLE 7

The list of 198 adhesins found in bacteria

| | |
|---|---|
| PapG (*E. coli*) | 12837502 |
| | 7407201 |
| | 7407207 |
| | 7407205 |
| | 147096 |

TABLE 7-continued

The list of 198 adhesins found in bacteria

| | |
|---|---:|
| | 4240529 |
| | 7407203 |
| | 42308 |
| | 7443327 |
| | 78746 |
| | 18265934 |
| | 26111419 |
| | 26250987 |
| | 26109826 |
| | 26249418 |
| | 13506767 |
| | 42301 |
| | 78745 |
| | 129622 |
| | 147092 |
| | 13506906 |
| | 7407209 |
| | 147080 |
| | 281926 |
| | 7407199 |
| | 147100 |
| | 78744 |
| SfaS (*E. coli*) | 477910 |
| | 264035 |
| | 42959 |
| | 134449 |
| | 96425 |
| FimH (*E. coli*) | 26251208 |
| | 26111640 |
| | 5524634 |
| | 29422425 |
| | 5524630 |
| | 29422435 |
| | 29422415 |
| | 10946257 |
| | 29422419 |
| | 11120564 |
| | 29422457 |
| | 11120562 |
| | 29422459 |
| | 5524632 |
| | 29422455 |
| | 29422453 |
| | 29422451 |
| | 29422449 |
| | 29422447 |
| | 29422445 |
| | 29422443 |
| | 29422437 |
| | 29422433 |
| | 29422431 |
| | 29422429 |
| | 29422427 |
| | 29422423 |
| | 29422421 |
| | 29422417 |
| | 729494 |
| | 1361011 |
| | 1790775 |
| | 3599571 |
| | 29422441 |
| | 12620398 |
| | 29422439 |
| | 5524628 |
| | 1787779 |
| | 1742472 |
| | 1742463 |
| | 15801636 |
| | 25321294 |
| | 12515169 |
| | 11120566 |
| | 24051859 |
| | 24112911 |
| | 13360484 |
| | 15800801 |
| | 15830279 |
| | 25392018 |
| | 25500156 |
| | 12514120 |
| | 1787173 |
| | 16128908 |
| | 16501811 |
| | 16759519 |
| | 24051219 |
| | 24112354 |
| | 30040724 |
| | 30062478 |
| | 6650093 |
| | 5524636 |
| | 1778448 |
| Intimin (*E. coli*) | 17384659 |
| | 4388530 |
| | 1389879 |
| | 15723931 |
| | 4323336 |
| | 4323338 |
| | 4323340 |
| | 4323342 |
| | 4323344 |
| | 4323346 |
| | 4323348 |
| | 4689314 |
| PrsG (*E. coli*) | 42523 |
| | 42529 |
| | 7443328 |
| | 7443329 |
| | 1172645 |
| HMW1 (Nontypeable *H. influenzae*) | 282097 |
| HMW2 (Nontypeable *H. influenzae*) | 5929966 |
| Hia (Nontypeable *H. influenzae*) | 25359682 |
| | 25359489 |
| | 25359709 |
| | 25359628 |
| | 25359414 |
| | 25359389 |
| | 21536216 |
| | 25359445 |
| HifE (*H. influenzae*) | 13506868 |
| | 13506870 |
| | 13506872 |
| | 13506874 |
| | 13506876 |
| | 3688787 |
| | 3688790 |
| | 3688793 |
| | 2126301 |
| | 1170264 |
| | 1170265 |
| | 533127 |
| | 535169 |
| | 3025668 |
| | 3025670 |
| | 3025672 |
| | 3025674 |
| | 642038 |
| MrkD (*K. pneumoniae*) | 127307 |
| FHA (*B. pertussis*) | 17154501 |
| Pertactin (*B. pertussis*) | 33571840 |
| YadA (*Y. enterocolitica*) | 10955604 |
| | 4324391 |
| | 28372996 |
| | 23630568 |
| | 32470319 |
| SpaP (*S. mutans*) | 26007028 |
| | 47267 |
| PAc (*S. mutans*) | 129552 |
| SspA (*Streptococcus gordonii*) | 25990270 |
| | 1100971 |
| CshA (*Streptococcus gordonii*) | 457707 |
| CshB (*Streptococcus gordonii*) | 18389220 |
| ScaA (*Streptococcus gordonii*) | 310633 |
| SspB (*Streptococcus gordonii*) | 25055226 |
| | 3220006 |
| SpaA (*Streptococcus sobrinus*) | 546643 |

TABLE 7-continued

The list of 198 adhesins found in bacteria

| | |
|---|---|
| PAg (*Streptococcus sobrinus*) | 217036 |
| | 47561 |
| Protein F (*Streptococcus pyogenes*) | 19224134 |
| PsaA (*Streptococcus pneumoniae*) | 18252614 |
| | 7920456 |
| | 7920458 |
| | 7920460 |
| | 7920462 |
| CbpA$^e$/SpsA/PbcA/PspC | 14718654 |
| (*Streptococcus pneumoniae*) | 2425109 |
| | 2576331 |
| | 2576333 |
| | 3153898 |
| | 9845483 |
| | 19548141 |
| FimA (*Streptococcus parasanguis*) | 97883 |
| SsaB (*Streptococcus sanguis*) | 97882 |
| EfaA (*Enterococcus faecalis*) | 493017 |
| FnbA (*Staphylococcus aureus*) | 120457 |
| FnbB (*Staphylococcus aureus*) | 581562 |
| | 21205592 |
| | 13702452 |
| BabA (*Helicobacter pylori*) | 13309962 |
| | 13309964 |
| | 13309966 |
| | 13309968 |
| | 13309970 |
| | 13309972 |
| | 13309974 |
| | 13309976 |
| | 13309978 |
| | 13309980 |
| | 13309982 |
| | 13309984 |
| | 13309986 |
| | 13309988 |
| | 13309990 |
| | 13309992 |
| | 13309994 |

Advantages:
1. The method helps in discovering putative adhesins, which are of great importance in drug discoveries and preventive therapeutics.
2. The method is useful in predicting the adhesive nature of even unique proteins, because it is independent of the homology of the query proteins with other proteins.
3. This method is easy to use. For calculating the output, only the amino acid sequence is required as input. No other information is required to get the information about its adhesive nature.

REFERENCES MAY BE MADE TO

1. Andrea, T. A., Kalayeh, H. (1991) Applications of neural networks in quantitative structure-activity relationships of dihydrofolate reductase inhibitors. J. Med. Chem. 34, 2824-2836.
2. Altschul S F, Gish W, Miller W, Myers E W, Lipman D J. (1990) Basic local alignment search tool. J Mol Biol. 215 (3), 403-410.
3. Bassinet L, Gueirard P, Maitre B, Housset B, Gounon P, Guiso N. (2000) Role of adhesins and toxins in invasion of human tracheal epithelial cells by Bordetella pertussis. Infect Immun. 68(4), 1934-1941.
4. Bock, K., et al. (1985). Specificity of binding of a strain of uropathogenic *Escherichia coli* to Gal alpha 1-4Gal-containing glycosphingolipids. J. Biol. Chem. 260, 8545-8551.
5. Brendel, V., Bucher, P., Nourbakhsh, I. R., Edwin Blaisdell, B., and Karlin, S. (1992) Methods and algorithms for statistical analysis of protein sequences: Proc. Natl. Acad. Sci. USA 89, 2002-2006.
6. Brennan, M. J., Delogu, G., Chen, Y., Bardarov, S., Kriakov, J., Alavi, M., Jacobs, W. R., (2001).
7. Evidence that Mycobacterial PE_PGRS proteins are cell surface constituents that influence interactions with other cells. Infect. Immun, 69, 7326-7333.
8. De B K, Woolfitt A R, Barr J R, Daneshvar M I, Sampson J S, Ades E W, Carlone G M. (2003) Analysis of recombinant acylated pneumococcal surface adhesin A of *Streptococcus pneumoniae* by mass spectrometry. Arch Biochem Biophys. 15, 419(2), 147-157.
9. Egland P G, Du L D, Kolenbrander P E (2001) Identification of independent *Streptococcus gordonii* SspA and SspB functions in coaggregation with Actinomyces naeslundii. Infect Immun. 69(12), 7512-7516
10. Finlay, B. B. and Falkow, S. (1997) Common themes in microbial pathogenicity revisited. Microbiol. Mol. Biol. Rev. 61, 136-169,
11. Fraser, C. M., Eisen, J., Fleischmann, R. D., Ketchum, K. A., Peterson, S. (2000) Comparative genomics and understanding of microbial biology. Emerg. Infect. Dis. 6,505-6512
12. Halperin, S. A., Scheifele, D., Mills, E., Guasparini, R., Humphreys, G., Barreto, L., Smith, B. (2003) Nature, evolution, and appraisal of adverse events and antibody response associated with the fifth consecutive dose of a five-component acellular pertussis-based combination vaccine. Vaccine 21, 2298-2306.
13. Hartford O, McDevitt D, Foster T J. (1999) Matrix-binding proteins of *Staphylococcus aureus*: functional analysis of mutant and hybrid molecules. Microbiology. 145 (Pt 9), 2497-2505.
14. Hobohm, U. and Sander, C. (1995) A sequence property approach to searching protein databases. J. Mol. Biol. 251, 390-399.
15. Ide T, Michgehl S, Knappstein S. Heusipp G, Schmidt M A. (2003) Differential modulation by Ca2+ of type III secretion of diffusely adhering enteropathogenic *Escherichia coli*. Infect Immun. 71(4), 1725-1732.
16. Langermann S et al. (2000) Vaccination with FimH adhesin protects cynomolgus monkeys from colonization and infection by uropathogenic *Escherichia coli*. J. Infect. Dis. 181, 774-778.
17. Lowe A. M., Lambert, P. A., Smith, A. W. (1995) Cloning of an *Enterococcus faecalis* endocarditis antigen: homology with adhesins from some oral streptococci. Infect Immun. 63, 703-706.
18. Maurer, L., Orndorff, P. (1987). Identification and characterization of genes determining receptor binding and pilus length of Escherichia coli type 1 pili. J. Bacteriol. 169, 640-645
19. Marchler-Bauer A, Panchenko A R, Shoemaker B A, Thiessen P A, Geer L Y, Bryant S H. (2002) CDD: a database of conserved domain alignments with links to domain three-dimensional structure. Nucleic Acids Res. 1, 30(1), 281-283.
20. Neubauer H, Hensel A, Aleksic S, Meyer H. (2000) Evaluation of a *Yersinia* adhesion gene (yadA) specific PCR for the identification of enteropathogenic *Yersinia enterocolitica*. Int J Food Microbiol. 15, 57(3),-225-227.
21. Nishikawa, K., Kubota, Y. and Ooi, T. (1983) Classification of proteins into groups based on amino acid composition and other characters. II. grouping into four types. J. Biochem. 94, 997-1007.

22. Peregrin-Alvarez, J. M., Tsoka, S., Ouzounis, C. A. (2003) The phylogenetic extent of metabolic enzymes and pathways. Genome Res. 13, 422-427.
23. Prinz, C., Hafsi, N. Voland, P. (2003) Helicobacter pylori virulence factors and the host immune response: implications for therapeutic vaccination. Trends in Microbiol. 11, 134-138.
24. Rapola, S., Jäntti, V., Eerola, M., Helena Mäkelä, P., Käyhty, H., Kilpi, T. (2003).Anti-PsaA and the risk of pneumococcal AOM and carriage. Vaccine 21,3608-3613.
25. Rison, S. C., Teichmann, S. A., Thornton, J. M. (2002) Homology, pathway distance and chromosomal localization of the small molecule metabolism enzymes in *Escherichia coli*. J. Mol. Biol. 318, 911-932
26. Sperandio V, Bailey C, Giron-J A, DiRita V J, Silveira W, Vettore A L, Kaper J B. (1996) Cloning and characterization of the gene encoding the OmpU outer membrane protein of Vibrio cholerae. Infect Immun. 64(12), 5406-5409.
27. St Geme J W 3rd, Cutter D. (2000) The *Haemophilus influenzae* Hia adhesin is an autotransporter protein that remains uncleaved at the C terminus and fully cell associated. J Bacteriol. 182(21), 6005-6013.
28. Thompson, J. D., Higgins,. D. G., Gibson, T. J. (1994) CLUSTAL W: improving the sensitivity of progressive multiple sequence alignment through sequence weighting, position-specific gap penalties and weight matrix choice. Nucleic Acids Res. 22, 4673-4680
29. Van Schilfgaarde M, van Ulsen P, Eijk P, Brand M, Stam M, Kouame J, van Alphen L, Dankert J. (2000) Characterization of adherence of nontypeable *Haemophilus influenzae* to human epithelial cells. Infect Immun. 68(8), 4658-4665.
30. Wizemann, T. M., Adamou, J. E., Langermann, S. (1999). Adhesins as targets for vaccine development. Emerg. Infect. Dis. 5, 395-403,
31. Wolf, Y. I., Rogozin, I. B., Kondrashov, A. S., and Koonin, E. V. (2001) Genome alignment, evolution of prokaryotic genome organization and prediction of gene function using genomic context. Genome Res.11, 356-372
32. Yu J, Leung W K, Go M Y, Chan M C, To K F, Ng E K, Chan F K, Ling T K, Chung S C, Sung J J. (2002) Relationship between Helicobacter pylori babA2 status with gastric epithelial cell turnover and premalignant gastric lesions. Gut. 51(4), 480-484.
33. Zuegge, J., Ralph, S., Schmuker, M., McFadden, G. I., Schneider, G. (2001) Deciphering apicoplast targeting signals—feature extraction from nuclear-encoded precursors of Plasmodium falciparum apicoplast proteins. Gene 280, 19-26.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07424370B2). An electronic copy of the "Sequence Listing" will also be available from the USPTO upon request and payment of the fee set forth in 37 CFR 1.19(b)(3).

The invention claimed is:

1. A computational method for identifying adhesin proteins, said method comprising steps of:
  a. computing the sequence-based defined attributes of protein sequences using five attribute modules of Software for Prediction of Adhesin and Adhesin-like proteins using Neural Networks (SPAAN), (i) amino acid frequencies, (ii) multiplet frequency, (iii) dipeptide frequencies of NG, RE, TN, NT, GT, TT, DE, ER, RR, RK, RI, AT, TS, IV, SG, GS, TG, GN, VI and HR, (iv) charge composition, and (v) hydrophobic composition,
  b. training artificial neural Network (ANN), one network for each of the computed five attributes by feeding the input data into the input layer of neurons,
  c. identifying as an adhesin a protein having a weighted average probability of being an adhesin ($P_{ad}$) value (optimal threshold) of $\geq 0.51$, and
  d. outputting sequence of identified protein to the user.

2. A method as claimed in claim 1, wherein the protein sequences are obtained from pathogens, eukaryotes, and multicellular organisms.

3. A method as claimed in claim 1, wherein the protein sequences are obtained from the pathogens selected from a group of organisms comprising *Escherichia coli, Haemophilus influenzae, Helicobacterpylori, Mycoplasma pneumoniae, Mycobacterium tuberculosis, Rickettsiae prowazekii, Porphyromonas gin givalis, Shigellaflexneri, Streptococcus mutans, Streptococcus pneumoniae, Neisseria meningitides, Streptococcus pyo genes, Treponema pallidum* and Severe Acute Respiratory Syndrome associated human coronavirus (SARS).

4. A method as claimed in claim 1, wherein the method is a non-homology method incorporating compositional properties and trained artificial neural network.

5. A method as claimed in claim 1, wherein the method uses 105 compositional properties of the protein sequences consisting of 20 properties each of amino acid frequencies, of multiplet frequencies, of dipeptide frequencies, of charge composition and 25 properties of hydrophobic composition.

6. A method as claimed in claim 1, wherein the method shows sensitivity of about 90% wherein sensitivity is greater than 90% for a Pad value above the optimal threshold.

7. A method as claimed in claim 1, wherein the method shows specificity of 100% wherein specificity is 100% for a Pad value above the optimal threshold.

8. A method as claimed in claim 1, wherein the method identifies adhesins from phylogenetically distantly related organisms.

9. A method as claimed in claim 1, wherein the neural network has multi-layer feed forward topology, consisting of an input layer, one hidden layer, and an output layer.

10. A method as claimed in claim 9, wherein the number of neurons in the input layer are equal to the number of input data points for each attribute.

11. A method as claimed in claim 1, wherein the "$P_{ad}$" is a weighted linear sum of the probabilities one each from five networks.

12. A method as claimed in claim 1, wherein each trained network assigns a probability value of being an adhesin for the protein sequence.

13. A computer system for performing the method of claim 1, said system comprising a central processing unit, executing SPAAN program, giving probabilities based on different attributes using Artificial Neural Network and in built other programs of assessing attributes, all stored in a memory device accessed by CPU, a display on which the central processing unit displays the screens of the above mentioned programs in response to user inputs; and a user interface device.

* * * * *

UNITED STATES PATENT AND TRADEMARK OFFICE
CERTIFICATE OF CORRECTION

PATENT NO. : 7,424,370 B2 Page 1 of 1
APPLICATION NO. : 11/052554
DATED : September 9, 2008
INVENTOR(S) : Gaurav Sachdeva et al.

It is certified that error appears in the above-identified patent and that said Letters Patent is hereby corrected as shown below:

On the Title Page:

Add field -- (30) Feb. 6, 2004 (IN) 173/DEL/2004 --.

In the Specification:

At Column 1, line 11, "06/589,220" should be -- 60/589,227 --.

In the Claims:

At Column 37, line 64, "Helicobacterpylori" should be -- Helicobacter pylori --.

At Column 37, line 66, "gin givalis" should be -- gingivalis --.

At Column 37, line 66, "Shigellaflexneri" should be -- Shigella flexneri --.

At Column 38, line 39, "pyo genes" should be -- pyogenes --.

Signed and Sealed this

Twenty-third Day of December, 2008

JON W. DUDAS
*Director of the United States Patent and Trademark Office*